(12) United States Patent
Gudmundson et al.

(10) Patent No.: US 9,157,873 B2
(45) Date of Patent: Oct. 13, 2015

(54) METHOD AND APPARATUS FOR ASSESSING THE THREAT STATUS OF LUGGAGE

(75) Inventors: Dan Gudmundson, Quebec (CA); Luc Perron, Charlesbourg (CA)

(73) Assignee: OPTOSECURITY, INC., Québec, Québec (CA)

( * ) Notice: Subject to any disclaimer, the term of this patent is extended or adjusted under 35 U.S.C. 154(b) by 737 days.

(21) Appl. No.: 13/377,872

(22) PCT Filed: Jun. 15, 2010

(86) PCT No.: PCT/CA2010/000916
§ 371 (c)(1),
(2), (4) Date: Dec. 13, 2011

(87) PCT Pub. No.: WO2010/145016
PCT Pub. Date: Dec. 23, 2010

(65) Prior Publication Data
US 2012/0093367 A1    Apr. 19, 2012

Related U.S. Application Data

(60) Provisional application No. 61/186,998, filed on Jun. 15, 2009, provisional application No. 61/230,435, filed on Jul. 31, 2009.

(51) Int. Cl.
*G06K 9/00* (2006.01)
*G01N 23/04* (2006.01)
*G01V 5/00* (2006.01)

(52) U.S. Cl.
CPC ............ *G01N 23/046* (2013.01); *G01V 5/0008* (2013.01); *G01N 2223/419* (2013.01)

(58) Field of Classification Search
CPC .................................................... G01N 23/046

USPC ......................................................... 382/103
See application file for complete search history.

(56) References Cited

U.S. PATENT DOCUMENTS 3,342,397 A    9/1967    Duitsman
3,589,511 A    6/1971    Britt
(Continued)

FOREIGN PATENT DOCUMENTS

CA    2574402    1/2006
CA    2623812    5/2007
(Continued)

OTHER PUBLICATIONS

Examiner's Report mailed on Nov. 7, 2012 in connection with European patent application No. 08876865.0, 3 pages.
(Continued)

*Primary Examiner* — Gandi Thirugnanam

(57) ABSTRACT

A method and apparatus for assessing a threat status of a piece of luggage. The method comprises the steps of scanning the piece of luggage with penetrating radiation to generate image data and processing the image data with a computing device to identify one or more objects represented by the image data. The method also includes further processing the image data to compensate the image data for interaction between the object and the penetrating radiation to produce compensated image data and then determine the threat status of the piece of luggage.

52 Claims, 16 Drawing Sheets

(56) References Cited

U.S. PATENT DOCUMENTS

| | | | |
|---|---|---|---|
| 3,609,045 A | 9/1971 | Stein | |
| 3,673,394 A | 6/1972 | Hartmann | |
| 4,075,700 A * | 2/1978 | Blay | 382/131 |
| 4,392,237 A | 7/1983 | Houston | |
| 4,454,949 A | 6/1984 | Flum | |
| 4,497,065 A | 1/1985 | Tisdale et al. | |
| 4,709,333 A * | 11/1987 | Crawford | 600/425 |
| 4,727,562 A | 2/1988 | Belanger | |
| 4,864,142 A | 9/1989 | Gomberg | |
| 4,870,666 A | 9/1989 | Lonn et al. | |
| 4,927,022 A | 5/1990 | Wilson | |
| 4,962,515 A | 10/1990 | Kopans | |
| 4,974,247 A | 11/1990 | Friddell | |
| 4,985,906 A | 1/1991 | Arnold | |
| 5,027,378 A * | 6/1991 | Fujii et al. | 378/11 |
| 5,044,002 A | 8/1991 | Stein | |
| 5,056,124 A | 10/1991 | Kakimoto et al. | |
| 5,400,381 A | 3/1995 | Steude et al. | |
| 5,428,657 A | 6/1995 | Papanicolopoulos et al. | |
| 5,442,672 A | 8/1995 | Bjorkholm et al. | |
| 5,490,218 A | 2/1996 | Krug et al. | |
| 5,524,133 A | 6/1996 | Neale et al. | |
| 5,557,108 A | 9/1996 | Tumer | |
| 5,568,262 A | 10/1996 | LaChapelle et al. | |
| 5,600,303 A | 2/1997 | Husseiny et al. | |
| 5,600,700 A | 2/1997 | Krug et al. | |
| 5,602,890 A | 2/1997 | Gray et al. | |
| 5,692,029 A | 11/1997 | Husseiny et al. | |
| 5,768,334 A | 6/1998 | Maitrejean et al. | |
| 5,838,758 A * | 11/1998 | Krug et al. | 378/53 |
| 5,864,600 A | 1/1999 | Gray et al. | |
| 5,974,111 A | 10/1999 | Krug et al. | |
| 6,018,562 A | 1/2000 | Willson | |
| 6,026,171 A | 2/2000 | Hiraoglu et al. | |
| 6,041,132 A | 3/2000 | Isaacs et al. | |
| 6,054,712 A | 4/2000 | Komardin et al. | |
| 6,069,936 A | 5/2000 | Bjorkholm | |
| 6,078,642 A | 6/2000 | Simanovsky et al. | |
| 6,088,423 A | 7/2000 | Krug et al. | |
| 6,122,344 A | 9/2000 | Beevor | |
| 6,175,655 B1 | 1/2001 | George et al. | |
| 6,201,850 B1 | 3/2001 | Heumann | |
| 6,542,574 B2 | 4/2003 | Grodzins | |
| 6,654,445 B2 | 11/2003 | Shepherd et al. | |
| 6,707,381 B1 | 3/2004 | Maloney | |
| 6,707,879 B2 | 3/2004 | McClelland et al. | |
| 6,721,387 B1 | 4/2004 | Naidu et al. | |
| 6,721,391 B2 | 4/2004 | McClelland et al. | |
| 6,753,527 B1 | 6/2004 | Yamagishi et al. | |
| 6,763,083 B2 | 7/2004 | Fernandez | |
| 6,840,120 B2 | 1/2005 | Sakairi et al. | |
| 6,952,163 B2 | 10/2005 | Huey et al. | |
| 7,033,070 B2 | 4/2006 | Azami | |
| 7,065,175 B2 | 6/2006 | Green | |
| 7,092,485 B2 | 8/2006 | Kravis | |
| 7,149,339 B2 | 12/2006 | Veneruso | |
| 7,154,985 B2 | 12/2006 | Dobbs et al. | |
| 7,164,750 B2 | 1/2007 | Nabors et al. | |
| 7,257,188 B2 | 8/2007 | Bjorkholm | |
| 7,260,254 B2 | 8/2007 | Highnam et al. | |
| 7,274,768 B2 | 9/2007 | Green | |
| 7,317,390 B2 | 1/2008 | Huey et al. | |
| 7,355,402 B1 | 4/2008 | Taicher et al. | |
| 7,386,093 B2 | 6/2008 | Wu et al. | |
| 7,508,908 B2 | 3/2009 | Hu et al. | |
| 7,614,788 B2 | 11/2009 | Gatten | |
| 7,684,605 B2 * | 3/2010 | Klingenbeck-Regn | 382/132 |
| 7,727,567 B2 | 6/2010 | Heuft | |
| 7,787,681 B2 | 8/2010 | Zhang et al. | |
| 7,789,401 B2 | 9/2010 | Ambrefe, Jr. | |
| 7,840,360 B1 | 11/2010 | Micheels et al. | |
| 7,869,637 B2 * | 1/2011 | Baumgart et al. | 382/128 |
| 7,873,201 B2 | 1/2011 | Eilbert et al. | |
| 7,945,017 B2 | 5/2011 | Chen et al. | |
| 8,090,150 B2 | 1/2012 | Garms | |
| 8,116,428 B2 * | 2/2012 | Gudmundson et al. | 378/53 |
| 8,150,105 B2 | 4/2012 | Mian et al. | |
| 8,260,020 B2 | 9/2012 | Garms | |
| 8,831,331 B2 | 9/2014 | Gudmundson et al. | |
| 8,867,816 B2 | 10/2014 | Bouchard et al. | |
| 8,879,791 B2 | 11/2014 | Drouin et al. | |
| 2001/0033636 A1 | 10/2001 | Hartick et al. | |
| 2002/0097833 A1 | 7/2002 | Kaiser et al. | |
| 2003/0062373 A1 | 4/2003 | Holland | |
| 2004/0016271 A1 | 1/2004 | Shah et al. | |
| 2004/0101097 A1 | 5/2004 | Wakayama et al. | |
| 2004/0232092 A1 | 11/2004 | Cash | |
| 2004/0252024 A1 * | 12/2004 | Huey et al. | 340/540 |
| 2005/0036689 A1 | 2/2005 | Mahdavieh | |
| 2005/0058242 A1 * | 3/2005 | Peschmann | 378/57 |
| 2005/0078801 A1 | 4/2005 | Georgeson et al. | |
| 2005/0111618 A1 | 5/2005 | Sommer, Jr. et al. | |
| 2005/0117700 A1 * | 6/2005 | Peschmann | 378/57 |
| 2005/0173284 A1 | 8/2005 | Ambrefe, Jr. | |
| 2005/0193648 A1 | 9/2005 | Klein et al. | |
| 2005/0226360 A1 * | 10/2005 | Kaucic et al. | 378/4 |
| 2005/0238232 A1 | 10/2005 | Ying et al. | |
| 2006/0013464 A1 * | 1/2006 | Ramsay et al. | 382/132 |
| 2006/0022140 A1 * | 2/2006 | Connelly et al. | 250/338.1 |
| 2006/0054682 A1 | 3/2006 | de la Huerga | |
| 2006/0078085 A1 | 4/2006 | Zanker | |
| 2006/0086794 A1 | 4/2006 | Knowles et al. | |
| 2006/0098773 A1 * | 5/2006 | Peschmann | 378/57 |
| 2006/0115044 A1 | 6/2006 | Wu et al. | |
| 2006/0133566 A1 | 6/2006 | Li et al. | |
| 2006/0187221 A1 * | 8/2006 | Lakare et al. | 345/424 |
| 2006/0193434 A1 | 8/2006 | Green | |
| 2006/0203960 A1 | 9/2006 | Schlomka et al. | |
| 2006/0239402 A1 | 10/2006 | Hu et al. | |
| 2006/0257005 A1 | 11/2006 | Bergeron et al. | |
| 2007/0003009 A1 | 1/2007 | Gray | |
| 2007/0013519 A1 | 1/2007 | Chung et al. | |
| 2007/0041612 A1 | 2/2007 | Perron et al. | |
| 2007/0041613 A1 | 2/2007 | Perron et al. | |
| 2007/0058037 A1 * | 3/2007 | Bergeron et al. | 348/82 |
| 2007/0098142 A1 | 5/2007 | Rothschild et al. | |
| 2007/0132580 A1 | 6/2007 | Ambrefe, Jr. | |
| 2007/0133743 A1 | 6/2007 | Johnson et al. | |
| 2007/0152033 A1 | 7/2007 | Hind et al. | |
| 2007/0168467 A1 * | 7/2007 | Hu et al. | 709/219 |
| 2007/0192850 A1 | 8/2007 | Cowburn | |
| 2007/0217571 A1 | 9/2007 | Teslyar et al. | |
| 2007/0297560 A1 | 12/2007 | Song et al. | |
| 2008/0056443 A1 | 3/2008 | Hu et al. | |
| 2008/0062262 A1 | 3/2008 | Perron et al. | |
| 2008/0063140 A1 * | 3/2008 | Awad | 378/57 |
| 2008/0116267 A1 | 5/2008 | Barber | |
| 2008/0138475 A1 | 6/2008 | Heuft | |
| 2008/0152082 A1 | 6/2008 | Bouchard et al. | |
| 2008/0167552 A1 | 7/2008 | Bouchevreau et al. | |
| 2008/0170660 A1 | 7/2008 | Gudmundson et al. | |
| 2008/0181473 A1 | 7/2008 | Garty et al. | |
| 2008/0240578 A1 * | 10/2008 | Gudmundson et al. | 382/218 |
| 2008/0253627 A1 * | 10/2008 | Boyden et al. | 382/128 |
| 2008/0283761 A1 * | 11/2008 | Robinson et al. | 250/370.09 |
| 2008/0312768 A1 | 12/2008 | Ewing et al. | |
| 2009/0003514 A1 * | 1/2009 | Edic et al. | 378/10 |
| 2009/0060135 A1 | 3/2009 | Morton | |
| 2009/0123051 A1 * | 5/2009 | Tamai et al. | 382/132 |
| 2009/0146061 A1 | 6/2009 | Manneschi | |
| 2009/0168963 A1 | 7/2009 | Harding | |
| 2009/0175411 A1 * | 7/2009 | Gudmundson et al. | 378/57 |
| 2009/0180591 A1 * | 7/2009 | Baumgart | 378/98.12 |
| 2009/0196396 A1 | 8/2009 | Doyle et al. | |
| 2009/0252295 A1 * | 10/2009 | Foland | 378/98.12 |
| 2010/0027741 A1 | 2/2010 | Doyle et al. | |
| 2010/0046704 A1 | 2/2010 | Song et al. | 378/57 |
| 2010/0074483 A1 * | 3/2010 | Janes | 382/128 |
| 2010/0127169 A1 | 5/2010 | Whittum et al. | 250/306 |
| 2010/0208972 A1 * | 8/2010 | Bouchard et al. | 382/132 |
| 2010/0220910 A1 | 9/2010 | Kaucic et al. | |
| 2010/0277312 A1 * | 11/2010 | Edic et al. | 340/540 |
| 2010/0284514 A1 | 11/2010 | Zhang et al. | |
| 2010/0329532 A1 * | 12/2010 | Masuda et al. | 382/132 |

(56) References Cited

U.S. PATENT DOCUMENTS

| | | |
|---|---|---|
| 2011/0007870 A1 | 1/2011 | Roux et al. |
| 2011/0172972 A1* | 7/2011 | Gudmundson et al. ............ 703/1 |
| 2011/0243299 A1* | 10/2011 | Sugita et al. .................... 378/19 |
| 2012/0093367 A1* | 4/2012 | Gudmundson et al. ....... 382/103 |
| 2012/0275646 A1 | 11/2012 | Drouin et al. |
| 2014/0198899 A1* | 7/2014 | Ziskin et al. .................... 378/53 |
| 2014/0211980 A1 | 7/2014 | Bouchard et al. |
| 2014/0241495 A1 | 8/2014 | Gudmundsun et al. |
| 2014/0321729 A1 | 10/2014 | Gudmundsen et al. |
| 2015/0010128 A1 | 1/2015 | Drouin et al. |

FOREIGN PATENT DOCUMENTS

| | | |
|---|---|---|
| CA | 2651728 | 4/2008 |
| CA | 2692662 | 3/2010 |
| CA | 2709468 | 3/2010 |
| CA | 2696031 | 5/2010 |
| CA | 2676913 | 11/2010 |
| CA | 2666838 | 12/2010 |
| CA | 2700553 | 4/2011 |
| CA | 2690163 | 8/2011 |
| EP | 2189785 | 5/2010 |
| EP | 2696196 | 2/2012 |
| EP | 2696196 | 2/2014 |
| EP | 2331944 | 3/2014 |
| EP | 2334565 | 3/2014 |
| GB | 2420683 | 5/2006 |
| GB | 2441551 | 3/2008 |
| JP | 2006214725 | 8/2006 |
| WO | WO94/12855 | 6/1994 |
| WO | WO9802763 | 1/1998 |
| WO | WO99/45371 | 9/1999 |
| WO | WO03/052398 | 6/2003 |
| WO | WO 2004/054329 | 6/2004 |
| WO | WO2006/119603 | 11/2006 |
| WO | WO2008/009134 | 1/2008 |
| WO | WO2008019473 | 2/2008 |
| WO | WO2008/034232 | 3/2008 |
| WO | WO2008/036456 | 3/2008 |
| WO | WO2008/040119 | 4/2008 |
| WO | WO2008/119151 | 10/2008 |
| WO | WO2009/024818 | 2/2009 |
| WO | WO2009/043145 | 4/2009 |
| WO | WO2009/046529 | 4/2009 |
| WO | WO2009/114928 | 9/2009 |
| WO | WO2009/127353 | 10/2009 |
| WO | WO2010/025538 | 3/2010 |
| WO | WO2010/025539 | 3/2010 |
| WO | WO2010/028474 | 3/2010 |
| WO | WO2010/145016 | 12/2010 |

OTHER PUBLICATIONS

Examiner's Report mailed on Jan. 16, 2013 in connection with Canadian patent application No. 2,697,586, 3 pages.
Examiner's Report mailed on Feb. 4, 2013 in connection with Canadian patent application No. 2,677,439, 2 pages.
Non-Final Office Action issued on Mar. 1, 2013 in connection with U.S. Appl. No. 12/681,826, 32 pages.
Non-Final Office Action issued on Feb. 28, 2013 in connection with U.S. Appl. No. 13/063,869, 52 pages.
Restriction Requirement issued on Mar. 11, 2013 in connection with U.S. Appl. No. 12/680,625, 6 pages.
Notice of Allowance issued on Dec. 2, 2013 in connection with U.S. Appl. No. 12/680,625—9 pages.
Extended European Search Report issued on Dec. 18, 2013 in connection with European patent application No. 13191619.9—6 pages.
Notice of Allowance issued on Jan. 16, 2014 in connection with U.S. Appl. No. 13/313,635—10 pages.
Notice of Allowance issued on Feb. 21, 2014 in connection with U.S. Appl. No. 12/864,988—7 pages.
Notice of Allowance issued on Mar. 17, 2014 in connection with U.S. Appl. No. 13/387,578—8 pages.
European Search Report mailed on Apr. 14, 2014 in connection with Europeant Patent Application No. 10788557.6—8 pages.
International Search Report mailed on Jan. 10, 2008 in connection with International Patent Application PCT/CA2007/001658, 6 pages.
Written Opinion of the International Searching Authority mailed on Jan. 10, 2008 in connection with International Patent Application PCT/CA2007/001658, 12 pages.
Informal Communication with the Applicant mailed on Sep. 22, 2008 in connection with International Patent Application PCT/CA2007/001658, 4 pages.
International Preliminary Report on Patentability mailed on Dec. 17, 2008 in connection with International Patent Application PCT/CA2007/001658, 7 pages.
International Search Report mailed on Jan. 14, 2008 in connection with International Patent Application PCT/CA2007/001749, 4 pages.
Written Opinion of the International Searching Authority mailed on Jan. 14, 2008 in connection with International Patent Application PCT/CA2007/001749, 4 pages.
International Search Report mailed on Nov. 20, 2008 in connection with International Patent Application PCT/CA2008/001591, 6 pages.
Written Opinion of the International Searching Authority mailed on Nov. 20, 2008 in connection with International Patent Application PCT/CA2008/001591, 6 pages.
International Search Report mailed on Dec. 4, 2008 in connection with International Patent Application PCT/CA2008/001721, 5 pages.
Written Opinion of the International Searching Authority mailed on Dec. 4, 2008 in connection with International Patent Application PCT/CA2008/001721, 5 pages.
International Search Report mailed on Dec. 5, 2008 in connection with International Patent Application PCT/CA2008/001792, 5 pages.
Written Opinion of the International Searching Authority mailed on Dec. 5, 2008 in connection with International Patent Application PCT/CA2008/001792, 5 pages.
International Search Report mailed on Jun. 4, 2009 in connection with International Patent Application PCT/CA2008/002025, 5 pages.
Written Opinion of the International Searching Authority mailed on Jun. 4, 2009 in connection with International Patent Application PCT/CA2008/002025, 6 pages.
International Search Report mailed on Jul. 6, 2009 in connection with International Patent Application PCT/CA2009/000395, 4 pages.
Written Opinion of the International Searching Authority mailed on Jul. 6, 2009 in connection with International Patent Application PCT/CA2009/000395, 4 pages.
International Search Report mailed on Aug. 6, 2009 in connection with International Patent Application PCT/CA2009/000401, 4 pages.
Written Opinion of the International Searching Authority mailed on Aug. 6, 2009 in connection with International Patent Application PCT/CA2009/000401, 8 pages.
International Search Report mailed on Nov. 10, 2009 in connection with International Patent Application PCT/CA2009/000811, 7 pages.
Written Opinion of the International Searching Authority mailed on Nov. 10, 2009 in connection with International Patent Application PCT/CA2009/000811, 3 pages.
International Preliminary Report on Patentability mailed on Feb. 1, 2010 in connection with International Patent Application PCT/CA2008/001792, 3 pages.
International Preliminary Report on Patentability mailed on Apr. 15, 2010 in connection with International Patent Application PCT/CA2008/001721, 6 pages.
Written Opinion of the International Searching Authority mailed on Sep. 22, 2010 in connection with International Patent Application PCT/CA2010/000916, 6 pages.
International Search Report mailed on Sep. 22, 2010 in connection with International Patent Application PCT/CA2010/000916, 4 pages.
International Preliminary Report on Patentability mailed on Sep. 21, 2010 in connection with International Patent Application PCT/CA2008/001591, 7 pages.
Written Opinion of the International Searching Authority mailed on Nov. 19, 2010 in connection with International Patent Application PCT/CA2010/001200, 6 pages.
International Search Report mailed on Nov. 19, 2010 in connection with International Patent Application PCT/CA2010/001200, 5 pages.

(56) References Cited

OTHER PUBLICATIONS

International Preliminary Report on Patentability mailed on Jan. 12, 2011 in connection with International Patent Application PCT/CA2009/000401, 15 pages.
International Preliminary Report on Patentability mailed on Oct. 24, 2011 in connection with International Patent Application PCT/CA2010/000916, 17 pages.
Office Action mailed on Jul. 29, 2009 in connection with Canadian Patent Application 2,651,728, 6 pages.
Office Action mailed on Jul. 10, 2009 in connection with Canadian Patent Application 2,666,838, 3 pages.
Office Action mailed on Nov. 3, 2009 in connection with Canadian Patent Application 2,666,838, 5 pages.
Office Action mailed on Jan. 28, 2010 in connection with Canadian Patent Application 2,676,913, 2 pages.
Office Action mailed on Jan. 28, 2010 in connection with Canadian Patent Application 2,666,838, 5 pages.
Office Action mailed on Mar. 2, 2010 in connection with Canadian Patent Application 2,676,903 4 pages.
Office Action mailed on Mar. 19, 2010 in connection with Canadian Patent Application 2,651,728 2 pages.
Office Action mailed on Mar. 31, 2010 in connection with Canadian Patent Application 2,690,163—3 pages.
Office Action mailed on May 5, 2010 in connection with Canadian Patent Application 2,676,913—2 pages.
Office Action mailed on May 14, 2010 in connection with Canadian Patent Application 2,690,831—3 pages.
Office Action mailed on Jun. 7, 2010 in connection with Canadian Patent Application 2,692,662—3 pages.
Office Action mailed on Jun. 30, 2010 in connection with Canadian patent application 2,696,031—2 pages.
Office Action mailed on Jun. 28, 2010 in connection with Canadian patent application 2,697,525—3 pages.
Office Action mailed on Aug. 5, 2010 in connection with U.S. Appl. No. 12/385,253—18 pages.
Office Action mailed on Aug. 12, 2010 in connection with U.S. Appl. No. 12/311,522—17 pages.
Office Action mailed on Aug. 31, 2010 in connection with Canadian patent application 2,690,831—2 pages.
Office Action mailed on Aug. 31, 2010 in connection with Canadian patent application 2,692,662—3 pages.
Office Action mailed on Sep. 30, 2010 in connection with U.S. Appl. No. 12/311,031—8 pages.
Office Action mailed on Oct. 6, 2010 in connection with Canadian patent application 2,696,031—2 pages.
Office Action mailed on Oct. 29, 2010 in connection with Canadian Patent Application 2,651,728—6 pages.
Office Action mailed on Oct. 28, 2010 in connection with Canadian Patent Application 2,676,903—2 pages.
Office Action mailed on Nov. 2, 2010 in connection with Canadian Patent Application 2,690,163—1 page.
Office Action mailed on Nov. 17, 2010 in connection with Canadian Patent Application 2,709,468—2 pages.
Examiner's Report mailed on Jan. 31, 2011 in connection with Canadian Patent Application 2,697,525—2 pages.
Office Action mailed on Feb. 10, 2011 in connection with U.S. Appl. No. 12/680,622—10 pages.
Office Action mailed on Feb. 8, 2011 in connection with U.S. Appl. No. 12/385,253—14 pages.
Office Action mailed on Feb. 9, 2011 in connection with U.S. Appl. No. 12/311,522—11 pages.
Office Action mailed on Mar. 2, 2011 in connection with U.S. Appl. No. 12/311,031—9 pages.
Examiner's Report mailed on Mar. 29, 2011 in connection with Canadian Patent Application 2,725,626—5 pages.
Examiner's Report mailed on Mar. 29, 2011 in connection with Canadian Patent Application 2,690,831—2 pages.
Office Action mailed on Apr. 20, 2011 in connection with U.S. Appl. No. 12/311,031—20 pages.
Examiner's Report mailed on May 2, 2011 in connection with Canadian patent application 2,692,662—3 pages.
European Search Report mailed on Jun. 9, 2011 in connection with European patent application No. EP2007815851.6—6 Pages.
Notice of allowance mailed on May 5, 2011 in connection with U.S. Appl. No. 12/385,253—8 pages.
Notice of allowance mailed on May 6, 2011 in connection with U.S. Appl. No. 12/311,522—7 pages.
Notice of allowance mailed on May 6, 2011 in connection with U.S. Appl. No. 12/680,622—8 pages.
Examiner's Report mailed on Jul. 5, 2011 in connection with Canadian patent application 2,696,031—2 pages.
Examiner's Report issued on Jul. 19, 2011 in connection with Canadian patent application 2,651,728—2 pages.
Examiner's Report mailed on Aug. 10, 2011 in connection with Canadian Patent Application 2,725,626—4 pages.
Examiner's Report mailed on Sep. 2, 2011 in connection with Canadian Patent Application 2,737,075—3 pages.
Notice of allowance mailed on Sep. 15, 2011 in connection with U.S. Appl. No. 12/311,031.
Benjamin, R., "Object-Based 3D X-Ray Imaging for Second-line Security Screening", London, 1995, (Abstract).
PinPoint TM Threat Identification Software, http://www.guardiantechintl.com/security.php?npage=pinpoint, Jul. 25, 2005, 4 pages.
"Secure Flight Passenger Screening Program", http://www.globalsecurity.org/security/systems/passenger_screen.htm, Oct. 28, 2005, 6 pages.
Optosecurity, "Security Technology Overview: Advanced Vehicle Verification & Threat Identification", 1 page.
Airport Magazine, Solutions, Products, Services, vol. 7, Mar. 2006, 5 pages.
Page, D. L. et al., "Perception-based 3D Triangle Mesh Segmentation Using Fast Marching Watersheds.", Proc. Intl. Conf. on Computer Vision and Pattern Recognition, vol. II, pp. 27-32, Madison, WI, Jun. 2003.
Freud et al., "Simulation of X-ray NDT Imaging Techniques", Proceedings of the 15th World Conference on Non-Destructive Testing, Rome, Oct. 15-21, 2000, http://www.ndt.net/article/wcndt00/papers/idn256/idn256.htm, pages consulted on Dec. 3, 2009, 7 pages.
Gao et al., "Application of X-ray CT to liquid security inspection: System analysys and beam hardening correction", Nuclear Instruments & Methods in Physics Research, Section-A:Accelerators, Spectrometers, Detectors and Associated Equipement, Elsevier, Amsterdam, NL, vol. 579, No. 1, pp. 395-399, Aug. 8, 2007.
Xie et al., "Simulation of X-ray Imaging Systems for Luggage Inspection", Second Explosives Detection Symposium and Aviation Security Conference, Nov. 12-15, 1996, pp. 248-253.
U.S. Statutory Invention Registration No. H2001 H—Newman, Oct. 5, 2004.
International Preliminary Report on Patentability mailed on Nov. 22, 2011 in connection with International Patent Application PCT/CA2010/001200, 12 pages.
Dreisetel, Pia et al. "Detection of liquid explosives using tomosynthetic reconstruction in multiview dual-energy x-ray systems",1st EU Conference on the Detection of Explosives, held in Avignon, France, from Mar. 14-16, 2011.
Notice of intent to grant issued on Apr. 11, 2013 in connection with European patent application No. 08876865.0—5 pages.
Notice of intent to grant issued on May 14, 2013 in connection with European patent application No. 09810945.7—5 pages.
Restriction Requirement issued on Jun. 14, 2013 in connection with U.S. Appl. No. 12/864,988—6 pages.
Examiner's Report mailed on May 29, 2013 in connection with European Patent Application No. 09839849.8—6 pages.
Examiner's Report mailed on Jul. 22, 2013 in connection with Canadian Patent Application 2,737,075—3 pages.
Examiner's Report mailed on Jul. 23, 2013 in connection with Canadian Patent Application 2,677,439—2 pages.
Non-Final Office Action issued on Aug. 14, 2013 in connection with U.S. Appl. No. 12/680,625—9 pages.
Non-Final Office Action issued on Sep. 25, 2013 in connection with U.S. Appl. No. 13/313,635—7 pages.

(56) References Cited

OTHER PUBLICATIONS

Non-Final Office Action issued on Oct. 31, 2013 in connection with U.S. Appl. No. 12/864,988—14 pages.
Final Office Action issued on Nov. 14, 2013 in connection with U.S. Appl. No. 13/063,869—50 pages.
Xiang Li et al., "A numerical simulator in VC++ on PC for iterative image reconstruction", Journal of X-ray Science and Technology, vol. 11, No. 2, Jan. 1, 2003, pp. 61-70, XP055063644, issn: 0895-3996.
Search Report mailed on Feb. 17, 2012 in connection with European Patent Application No. 08835738.9—7 pages.
Search Report mailed on Feb. 1, 2012 in connection with European Patent Application No. 08876865.0—7 pages.
Search Report mailed on Jul. 18, 2012 in connection with European Patent Application No. 09839849.8—8 pages.
Examiner's Report mailed on Jul. 18, 2012 in connection with European Patent Application No. 09810945.7—4 pages.
Examiner's Report mailed on Aug. 31, 2012 in connection with European patent application No. 2007815851.6—6 pages.
Bottigli et al., "Voxel-based Monte Carlo Simulation of X-Ray imaging and spectroscopy experiments", Spectrochimia Acta. Part B: Atomic Spectroscopy, vol. 59, No. 10-11—Oct. 8, 2004, pp. 1747-1754, XP004598270.
Sluser M et al., "Model-based probabilistic relaxation segmentation applied to threat detection in airport x-ray imagery", Electrical and Computer Engineering, 1999 IEEE Canadian Conference on Edmonton, Alta., Canada, May 9-12, 1999, pp. 720-726, vol. 2, XP032158352.
Search Report mailed on Nov. 10, 2011 in connection with European Patent Application No. 09810945.7—7 pages.
European Search Report mailed on Apr. 14, 2014 in connection with European Patent Application No. 10788557.6—8 pages.
Notice of Allowance issued on Jun. 9, 2014, in connection with U.S. Appl. No. 12/864,988—7 pages.
Examiner's Report mailed on Jul. 9, 2014 in connection with European Patent Application No. 09839849.8—3 pages.
Examiner's Report mailed on Jun. 26, 2014 in connection with European Patent Application No. 07815851.6—4 pages.
Examiner's Report mailed on Jul. 15, 2014 in connection with Canadian Patent Application No. 2,677,439—2 pages.
Notice of Allowance issued on Jun. 25, 2014 in connection with U.S. Appl. No. 13/387,578—8 pages.
Examiner's Report mailed on Aug. 5, 2014 in connection with Canadian Patent Application No. 2,737,075—3 pages.
Restriction Requirement issued on Sep. 11, 2014 in connection with U.S. Appl. No. 14/244,213—6 pages.
Office Action issued on Nov. 20, 2014 in connection with U.S. Appl. No. 14/244,213, 10 pages.
Examiners Report issued on Apr. 9, 2015 in connection with European Patent Application 07815851.6, 3 pages.
Examiners Report issued on Apr. 7, 2015 in connection with Canadian Patent Application No. 2,697,586, 6 pages.
Notice of Allowance issued on Jul. 7, 2015 in connection with U.S. Appl. No. 14/496,676-8 pages.
Examiner's Report mailed on Jun. 29, 2015 in connection with Canadian Patent Application No. 2,677,439-3 pages.
Examiner's Report mailed on Jul. 17, 2015 in connection with Canadian Patent Application 2,737,075-6 pages.
Non-Final Office Action issued on Jul. 2, 2015 in connection with U.S. Appl. No. 13/063,869-37 pages.

* cited by examiner view 1

METHOD AND APPARATUS FOR ASSESSING THE THREAT STATUS OF LUGGAGE

CROSS-REFERENCE TO RELATED APPLICATIONS

This application is a National Phase Entry of international PCT patent application No. PCT/CA2010/000916 file on Jun. 15, 2010 by Optosecurity et al. designating the United States and claiming the benefit of priority under 35 USC §119(e) based on U.S. provisional patent application No. 61/186,998 filed Jun. 15, 2009 and based on U.S. provisional patent application No. 61/230,435 filed Jul. 31, 2009. The contents of the above noted applications are incorporated herein by reference.

FIELD OF THE INVENTION

The present invention relates to technologies for assessing the threat status of luggage. The invention has numerous applications; in particular it can be used for scanning luggage at airport or other security check points.

SUMMARY OF THE INVENTION

As embodied and broadly described herein, the invention provides a method and a system for assessing a threat status of a piece of luggage. The method comprises the steps of scanning the piece of luggage with penetrating radiation to generate image data and processing the image data with a computing device to determine the presence of an objet represented by the image data. The method also includes further processing the image data to compensate the image data for interaction between the object and the penetrating radiation to produce compensated image data and then determine the threat status of the piece of luggage on the basis of compensated image data.

As embodied and broadly described herein, the invention also provides a method and a system for assessing a threat status of a piece of luggage that contains an object. The method includes scanning the piece of luggage with X-rays to generate image data and provide a computing device programmed with software for execution by a CPU. The computing device simulating an interaction between the object and X-rays to compute X-rays attenuation information and processing the X-ray attenuation information to reduce a signature of the object in the image data and generate compensated image data. The threat status of the piece of luggage is determined on the basis of the compensated image data.

As embodied and broadly described herein the invention also provides a method for assessing a threat status of a piece of luggage containing a laptop computer. The method includes scanning the piece of luggage with penetrating radiation to generate image data and processing the image data with a computing device programmed with software for execution by a CPU, for:
i) identifying a portion of the image that conveys information about attenuation of X-rays due to interaction between the X-rays and the laptop computer;
ii) reduce a visual signature if the interaction in the identified portion of the image to produce compensated image data.

As embodied and broadly described herein, the invention also provides method and a system for visually enhancing an X-ray image to increase the likelihood of visually detecting the presence of explosive material hidden in an electronic device. The method includes scanning a piece of luggage containing an electronic device with X-rays to generate X-ray image data and process the X-ray image data with a computing device to:
i) identify a portion of the X-ray image that conveys information about attenuation of X-rays due to interaction between the X-rays and the electronic device and in the event the electronic device contains explosive material attenuation information due to interaction between X-rays and the explosive material;
ii) compensate the X-ray image data to reduce the contribution to the attenuation information within the portion due to the interaction between the electronic device and the X-rays.

As embodied and broadly described herein the invention also provides a system for assessing a threat status of a piece of luggage that contains an object. The system has an X-ray scanner for scanning the piece of luggage with X-rays to generate X-ray image data and a computing device programmed with software for execution by a CPU, for processing the X-ray image data to reduce a signature of the object in the X-ray image data and produce a compensated X-ray image data. The system also has a display device for displaying an image of the piece of luggage derived from the compensated X-ray image data. The computing device implements a user interface including a control, the computing device being responsive to actuation of the control to alter a degree of object signature reduction in the X-ray image.

A system for assessing a threat status of a piece of luggage that contains an object. The system has an X-ray scanner for scanning the piece of luggage with X-rays to generate X-ray image data and a computing device programmed with software for execution by a CPU, for processing the X-ray image data to reduce a signature of the object in the X-ray image data and produce a compensated X-ray image data. The system also has a display device for displaying an image of the piece of luggage derived from the compensated X-ray image data. The computing device implementing a user interface including a control, the computing device being responsive to actuation of the control to toggle the display device between a first mode and a second mode, the first mode and the second mode deferring by a degree of object signature reduction.

A system for assessing a threat status of a piece of luggage that contains an object having an X-ray scanner for scanning the piece of luggage with X-rays to generate X-ray image data and a computing device programmed with software for execution by a CPU, for processing the X-ray image data to reduce a signature of the object in the X-ray image data and produce a compensated X-ray image data. The computing device generates a composite image signal derived from the compensated X-ray image data including an overlay to illustrate a position of the object. The system also has a display device for displaying an image of the piece of luggage derived from the composite image signal.

As embodied and broadly described herein, the invention also provides a system for assessing a threat status of a piece of luggage that contains an object. The system including an X-ray scanner for scanning the piece of luggage with X-rays to generate X-ray image data and a computing device programmed with software for execution by a CPU, for processing the X-ray image data to reduce a visual presence of the object. The computing device implements a user interface including a control operable by a user to designate a location in the X-ray image where the object resides, the computing device being responsive to the control to processing the X-ray image data to reduce visual presence of the object at the location and generate compensated X-ray image data. The system also has a display device for displaying an image of the piece of luggage derived from the compensated X-ray image data.

BRIEF DESCRIPTION OF THE DRAWINGS

A detailed description of examples of implementation of the present invention is provided hereinbelow with reference to the following drawings, in which.

Figure 1:
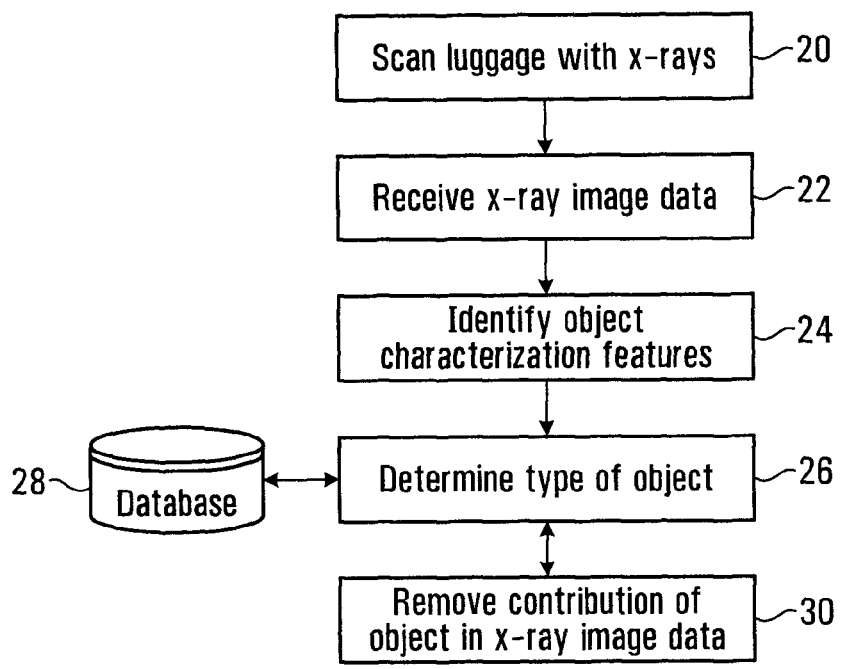
FIG. 1 is a flow chart of the method for performing threat assessment according to an example of implementation of the present invention.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

FIG. 1 illustrates a flowchart of a process performed according to a non-limiting example of implementation of the invention for conducting a security screening operation on luggage such as a suitcase.

Generally speaking, the process, which can be performed at a security checkpoint or at any other suitable location, would start with step 20, where the luggage is scanned with X-rays in order to derive X-ray attenuation data. The X-ray attenuation data conveys information about the interaction of the X-rays with the contents of the luggage. In a specific and non-limiting example of implementation, the X-ray attenuation data is contained in the X-ray image data, which is normally the output of an X-ray scan. Note that "X-ray image" data does not imply that the scanner necessarily produces an X-ray image for visual observation by an observer, such as the operator, on a display monitor. Examples of implementation are possible where the system can operate where the X-ray image data output by the X-ray scanner is not used to create an image on the monitor to be seen by the operator.

At step 22, the X-ray image data is output from the X-ray scanning apparatus and received by a suitable data processing device. The data processing device then performs suitable processing of the X-ray image data at step 24 which searches the X-ray image data for characterization features indicating the possible presence in the luggage of certain objects.

If characterization features are found in the X-ray image data the processing derives at step 26 properties of the object associated with the characterization features. The performance of step 26 may include interaction with a database 28 that maps respective objects or their characterization features and object properties. Examples of object properties include a nominal X-ray signature of the object such as the degree of X-ray attenuation and dimensions of the object among others.

At step 30 the object property derived at step 26 is used to compensate the X-ray image data such as to reduce or even eliminate the "presence" of the object in the X-ray image data. The thus compensated X-ray image data can then be processed to determine if the luggage is a security threat. The processing can be automatic, rely on a human operator or a combination of both. Automatic processing could involve a processing of the compensated attenuation information conveyed by the X-ray image data in order to determine the presence of prohibited materials, such as explosives, on the basis of material composition. Automatic processing could also involve a shape analysis of articles in the X-ray image to locate the presence of threatening articles, such as guns or stabbing objects.

A human operator can be involved in the threat assessment process by displaying the compensated image on a display to show the operator a "de-cluttered" view of the contents of the luggage, such that the operator can determine based on his/her judgement if a prohibited object is present in the luggage.

Both processes can also be run, in parallel or sequentially. In that scenario the involvement of the operator can be useful to validate the results of the automatic threat detection processing or to resolve cases where the automatic threat detection processing produces ambiguous results.

1) Scanning Luggage with X-rays

Figure 17:
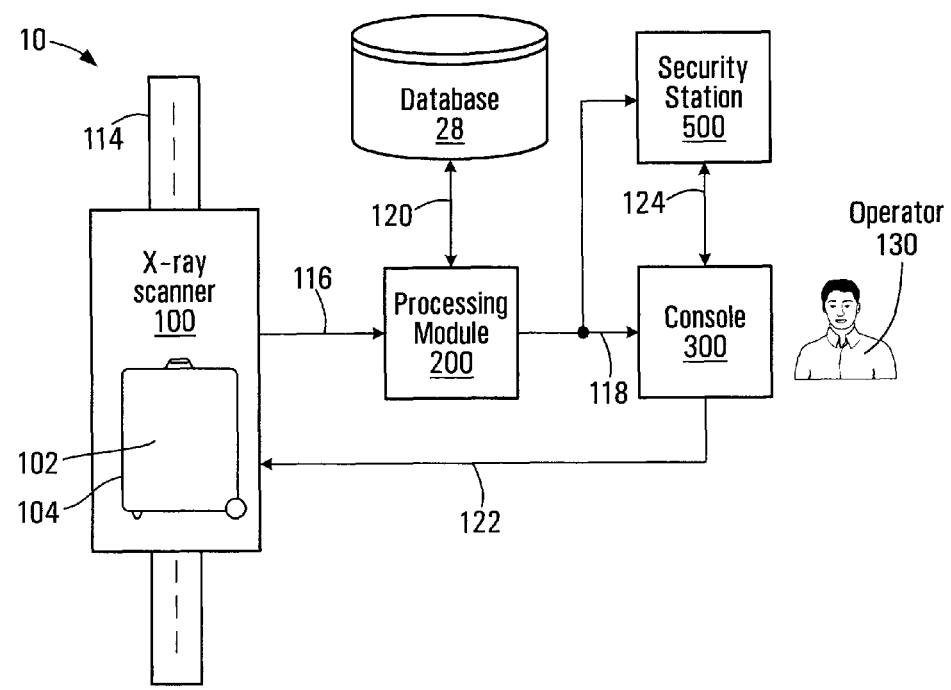
FIG. 17 a is a block diagram of an apparatus using X-rays to scan hand carried baggage at a security check point, according to a non-limiting example of implementation of the invention.

With reference to FIG. 17, there is shown a specific non-limiting example of a system 10 for use in screening luggage, in accordance with a non-limiting embodiment of the present invention. The system 10 comprises an X-ray scanner 100 that applies an X-ray screening process to a piece of luggage 104, such as a suitcase that is located within a screening area of the X-ray scanner 100. In an airport setting, a passenger may place the piece of luggage 104 onto a conveyor belt 114 that causes the piece of luggage 104 to enter the screening area of the X-ray scanner 100. The X-ray scanner 100 outputs an X-ray image data signal 116 to a processing module 200, best shown in FIG. 19.

The processing module 200 may be co-located with the X-ray scanner 100 or it may be remote from the X-ray scanner 100 and connected thereto by a communication link, which may be wireless, wired, optical, etc. The processing module 200 receives the X-ray image data signal 116 and executes the method briefly described in connection with FIG. 1 to produce de-cluttered X-ray image data. The processing module 200 has access to the database 28 via a communication link 120. The processing module 200 may be implemented using software, hardware, or a combination thereof.

In the example shown, the de-cluttered X-ray image data is directed to a console 300 and/or to a security station 500, where the X-ray image can be shown to an operator 130 or other security personnel. The console 300 can be embodied as a piece of equipment that is in proximity to the X-ray scanner 100, while the security station 500 can be embodied as a piece of equipment that is remote from the X-ray scanner 100. The console 300 may be connected to the security station 500 via a communication link 124 that may traverse a data network (not shown).

The console 300 and/or the security station 500 may comprise suitable software and/or hardware and/or control logic to implement a graphical user interface (GUI) for permitting interaction with the operator 130. Consequently, the console 300 and/or the security station 500 may provide a control link 122 to the X-ray scanner 100, thereby allowing the operator 130 to control motion (e.g., forward/backward and speed) of the conveyor belt 114 and, as a result, to control the position of the suitcase contents 102 within the screening area of the X-ray scanner 100.

Figure 18:
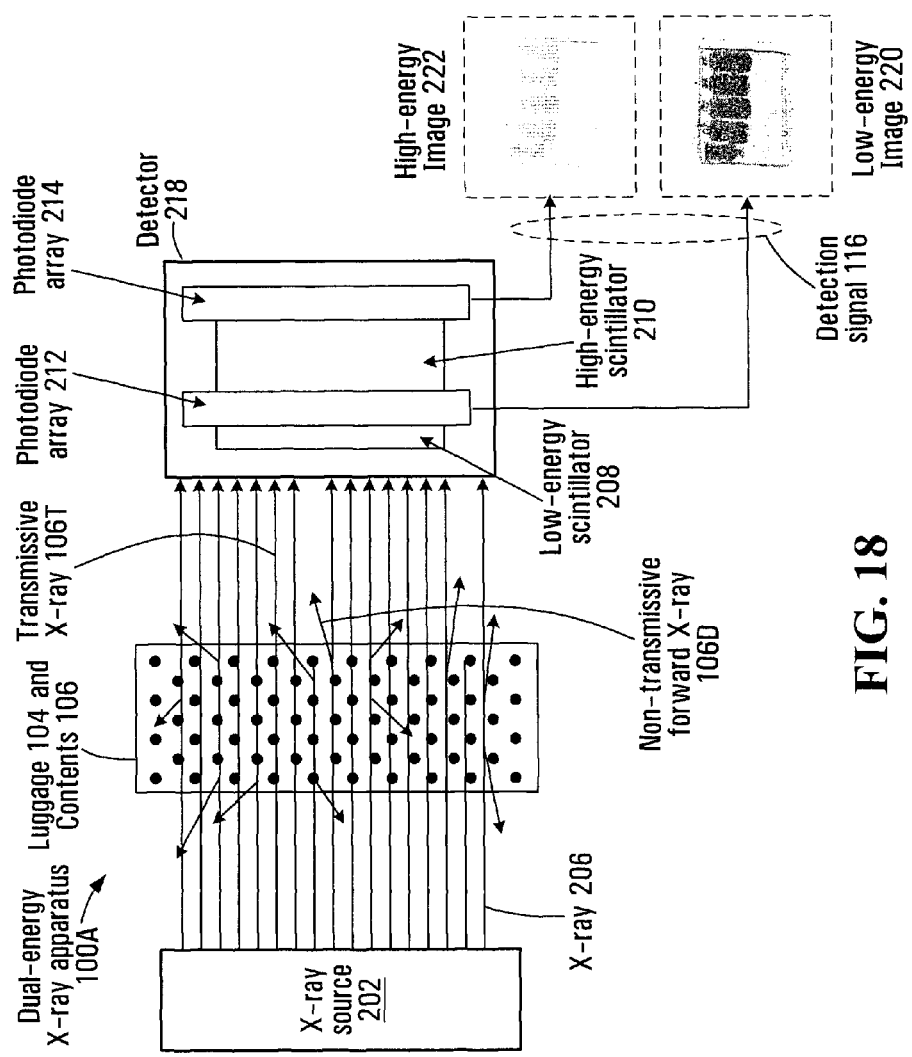
FIG. 18 is a schematical illustration of the X-ray scanner illustrating the different components thereof.

In accordance with a specific non-limiting embodiment, and with reference to FIG. 18, the X-ray scanner 100 is a dual-energy X-ray scanner 100A. However, persons skilled in the art will appreciate that the present invention is not limited to such an embodiment. Continuing with the description of the dual-energy X-ray scanner 100A, an X-ray source 202 emits X-rays 206 at two distinct photon energy levels, either simultaneously or in sequence. Example energy levels include 50 keV (50 thousand electron-volts) and 150 keV, although persons skilled in the art will appreciate that other energy levels are possible.

Generally speaking, X-rays are typically defined as electromagnetic radiation having wavelengths that lie within a range of 0.001 to 10 nm (nanometers) corresponding to photon energies of 120 eV to 1.2 MeV.

A detector 218 located generally along an extension of the path of the X-rays 206 receives photons emanating from the luggage 104. Some of the incoming photons (X-rays 206) will go straight through the luggage 104 while some will interact with the contents of the luggage 104. There are a number of interactions possible, such as:

The Rayleigh scattering (coherent scattering)
The photoelectric absorption (incoherent scattering)
The Compton scattering (incoherent scattering)
The pair production;
Diffraction (related to scattering)

Figure 20:
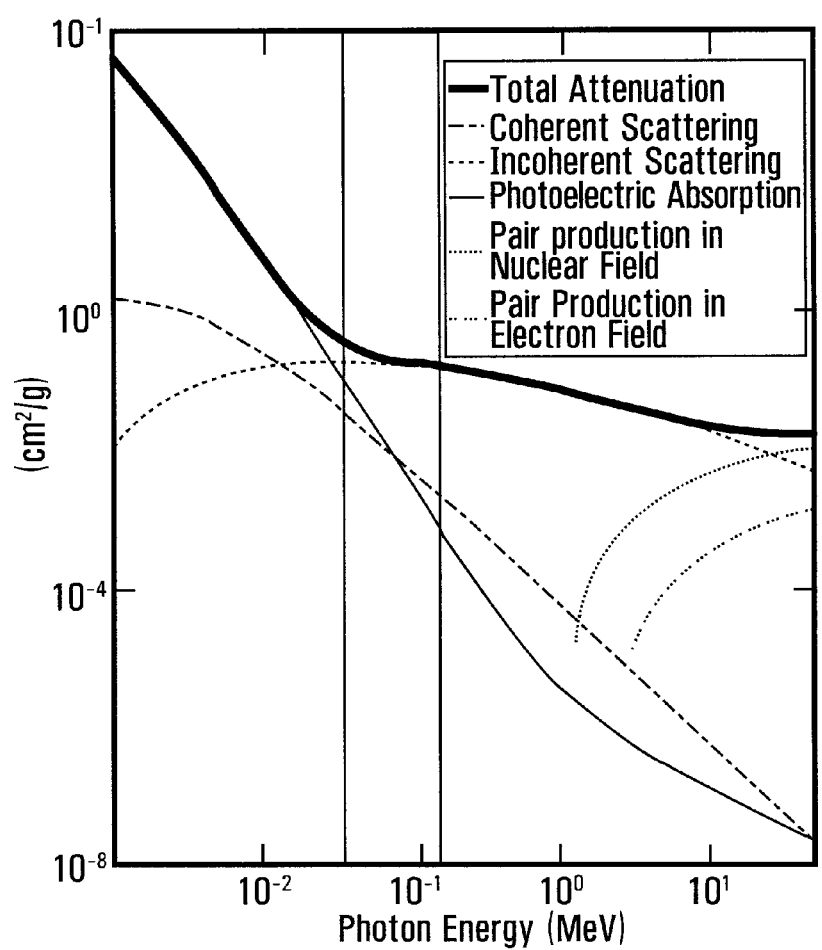
FIG. 20 is graph illustrating the total X-ray attenuation in H2O due to various X-ray matter interactions.

The total attenuation shown in the graph of FIG. 20 is the contribution of the various X-rays—matter interactions. In this example the matter is $H_2O$ but the attenuation profile for other materials is generally similar.

Figure 21:
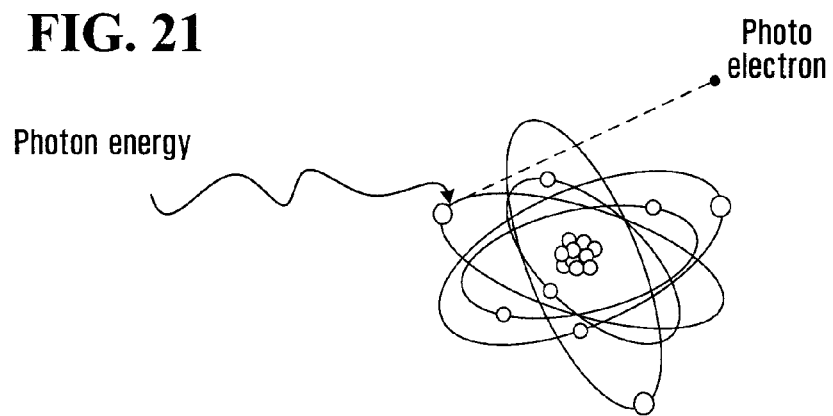
FIG. 21 is a generalized illustration of the photoelectric X-ray absorption process.

The photoelectric absorption (FIG. 21) of X-rays occurs when the X-ray photon is absorbed, resulting in the ejection of electrons from the shells of the atom, and hence the ionization of the atom. Subsequently, the ionized atom returns to the neutral state with the emission of whether an Auger electron or an X-ray characteristic of the atom. This subsequent X-ray emission of lower energy photons is however generally absorbed and does not contribute to (or hinder) the X-ray image making process. This type of X-ray interaction is dependent on the effective atomic number of the material or atom and is dominant for atoms of high atomic numbers. Photoelectric absorption is the dominant process for X-ray absorption up to energies of about 25 keV. Nevertheless, in the energy range of interest for security applications, the photoelectric effect plays a smaller role with respect to the Compton scattering, which becomes dominant.

Figure 22:
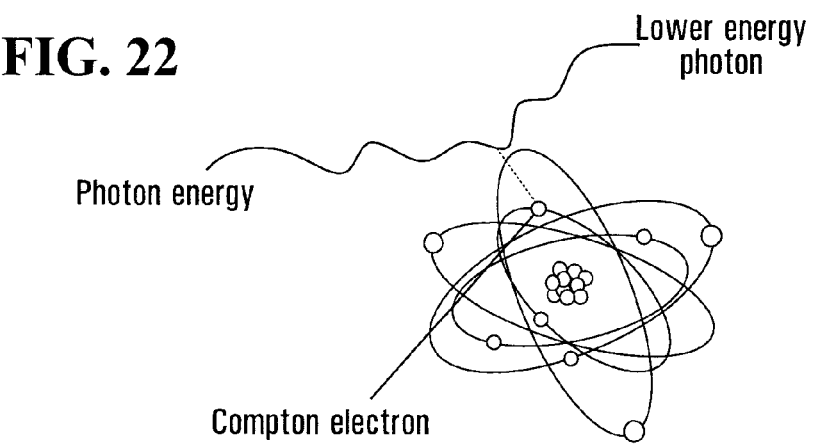
FIG. 22 is a generalized illustration of the Compton scattering effect.

Compton scattering (FIG. 22) occurs when the incident X-ray photon is deflected from its original path by an interaction with an electron. The electron gains energy and is ejected from its orbital position. The X-ray photon looses energy due to the interaction but continues to travel through the material along an altered path. Since the scattered X-ray photon has less energy, consequently it has a longer wavelength than the incident photon. The event is also known as incoherent scattering, because the photon energy change resulting from an interaction is not always orderly and consistent. The energy shift depends on the angle of scattering and not on the nature of the scattering medium. Compton scattering is proportional to material density and the probability of it occurring increases as the incident photon energy increases.

The diffraction phenomenon of the X-rays by a material with which they interact is related to the scattering effect described earlier. When the X-rays are scattered by the individual atoms of the material, the scattered X-rays may then interact and produce diffraction patterns that depend upon the internal structure of the material that is being examined.

The photons received by the detector 218 include photons that have gone straight through the suitcase 104 and its contents 102; these photons have not interacted in any significant matter with the suitcase 104. Others of the received photons have interacted with the suitcase 104 or its contents 102.

In accordance with a specific non-limiting embodiment of the present invention, the detector 218 may comprise a low-energy scintillator 208 and a high-energy scintillator 210. The low-energy scintillator 208 amplifies the intensity of the received photons such that a first photodiode array 212 can generate a low-energy image data 220. Similarly, the high-energy scintillator 210 amplifies the intensity of the received photons such that a second photodiode array 214 can generate a high-energy image data 222. The low-energy image data 220 and the high-energy image data 222 may be produced simultaneously or in sequence. In this example, the low-energy X-ray image data 220 and the high-energy X-ray image data 222 form the aforesaid X-ray image data signal 116.

Referring back to FIG. 17, the processing module 200 receives the X-ray image data signal 116 and processes the signal in conjunction with data contained in a database 28 to de-clutter the X-ray image and optionally perform an automatic threat assessment operation on the de-cluttered image.

Figure 19:
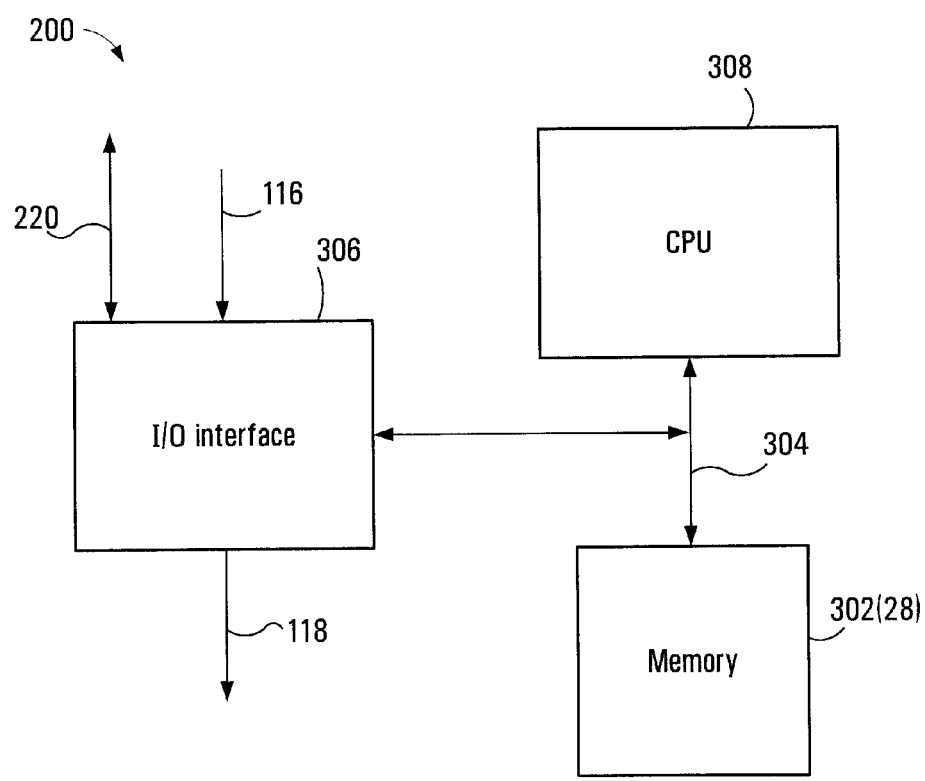
FIG. 19 is a block diagram of a processing module for use with an X-ray scanning apparatus to process the X-ray image data and perform X-ray image compensation to remove the contribution of objects shown in the image.

FIG. 19 is a high level block diagram of the processing module 200. The processing module 200 has a Central Processing Unit (CPU) 308 that communicates with a memory 302 over a data bus 304. The memory 302 stores the software that is executed by the CPU 308 and which defines the functionality of the processing module 200. The CPU 308 exchanges data with external devices through an Input/Output (I/O) interface 306. Specifically, the X-ray image data signal 116 is received at the I/O interface 306 and the data contained in the signal is processed by the CPU 308. The de-cluttered signal 118 that is generated by the CPU 308 is output to the console 308 and/or the security station 500 via the I/O interface 306. Also, communications between the database 28 and the processing module 200 are made via the I/O interface 306. Conceptually, the database 28 is shown as being part of the memory 302, although from an implementation perspective the database 28 can be remote from the storage medium in which is held the software code that defines the functionality of the processing module 200.

The example of implementation shown in FIG. 18 uses an X-ray scanning apparatus that produces X-ray image data representing a single view of the piece of luggage. The general configuration of this type of X-ray scanning apparatuses is shown in FIG. 2.

Figure 2:
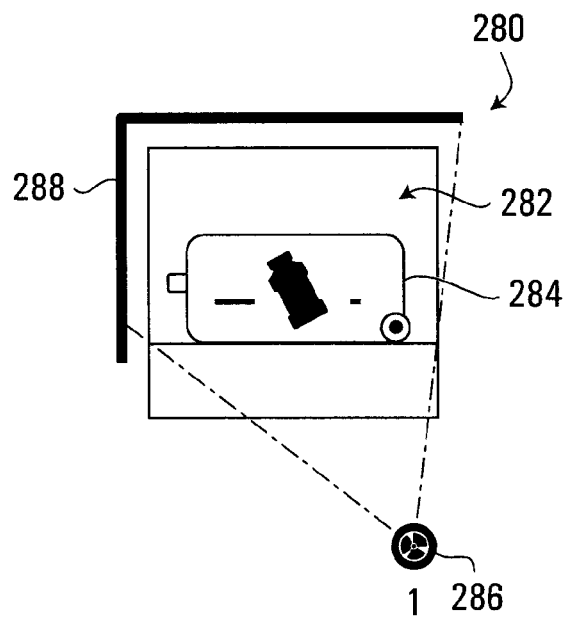
FIG. 2 is a schematical view of a single view X-ray scanning apparatus.
Figure 3:
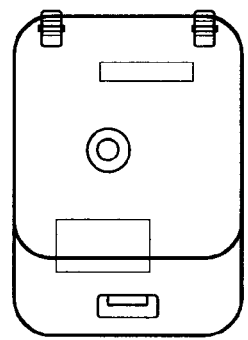
FIG. 3 is an example of an X-ray image obtained by the X-ray scanning apparatus of FIG. 2.

The X-ray scanning apparatus 280 includes a scanning area 282 in which is carried the piece of luggage 284 by the conveyor belt 114 (not shown in FIG. 2). An X-ray source 286 generates a fan-shaped X-ray beam that interacts with the contents of the luggage 284. The X-rays that pass through the piece of luggage 284 are picked up by an L-shaped sensor array 288. The X-ray data produced by the sensor array 288 is a single view representation of the piece of luggage 284, as the one shown in FIG. 3.

Figure 4:
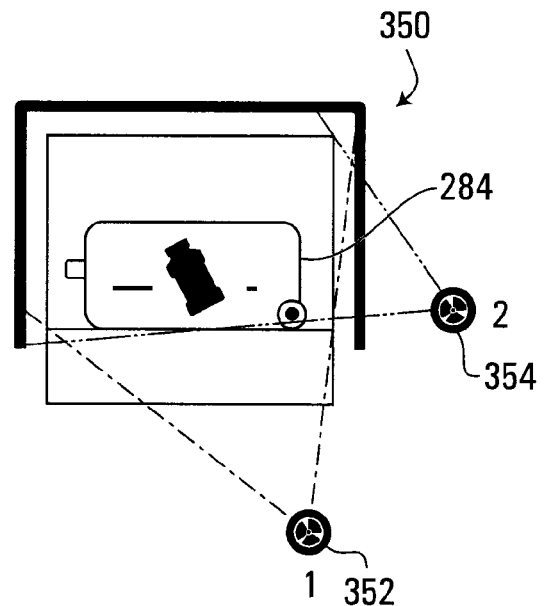
FIG. 4 is a schematical view of a dual view X-ray scanning apparatus.
Figure 5:
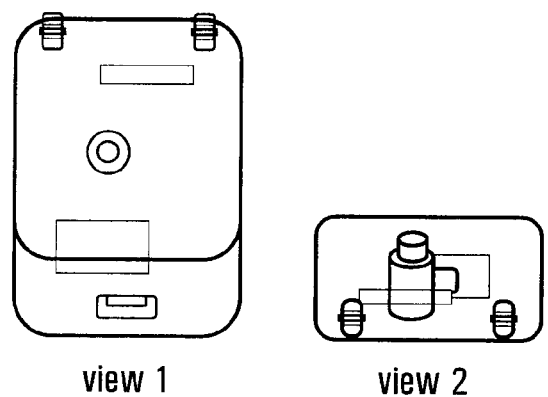
FIG. 5 is an example of X-ray images obtained by the X-ray scanning apparatus of FIG. 3.

FIG. 4 illustrates an X-ray scanning apparatus 350 that subjects the piece of luggage to two sources of X-ray radiation 352 and 354 oriented at an angle that can be in the order of 90 degrees. Other angular relationships are possible. This arrangement produces X-ray image data conveying representations of the piece of luggage 284 from two different perspectives or views as shown in FIG. 5. More specifically, the X-ray source 352 produces the view "View 1" in FIG. 5 while the X-ray source 354 produces the view "View 2" in FIG. 5.

Figure 6:
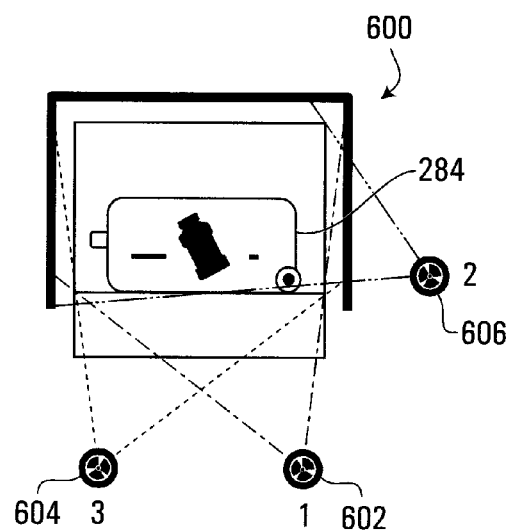
FIG. 6 is a schematical view of a three-view X-ray scanning apparatus.
Figure 7:
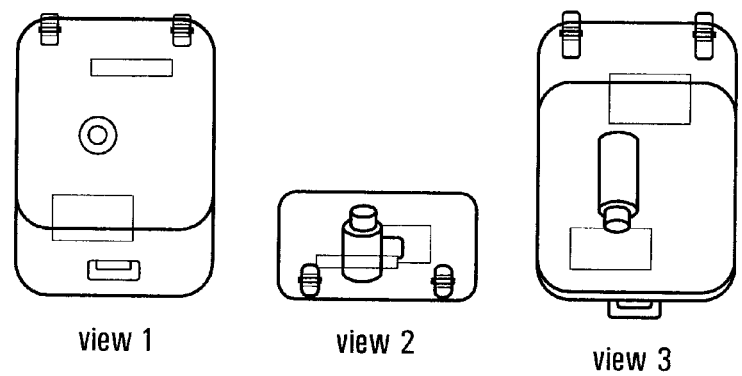
FIG. 7 is an example of X-ray images obtained by the X-ray scanning apparatus of FIG. 6.
Figure 9:
FIG. 9 is a more realistic X-ray image of the same piece of luggage shown in FIG. 8 but from the side.

FIG. 6 shows yet another possible example of an X-ray scanner 600 which uses three sources of X-ray radiation 602, 604 and 606. The X-ray sources 602, 604 and 606 are oriented at such an angular relationship as to produce X-ray image data conveying three different views of the piece of luggage 284. More specifically, the X-ray source 602 produces the view "View 1", the X-ray source 606 produces the view "View 2" and the X-ray source 604 produces the view "View 3" in FIG. 7.

2) Identify Object Characterization Features

In one specific and non-limiting example of implementation the X-ray image data is processed to determine if it contains object characterization features which indicate the presence of certain objects in the piece of luggage. Several possible examples of implementation are possible. Those examples of implementation are discussed below.

(a) Determining Object Characterization Features in X-ray Data Conveying a Single View of the Piece of Luggage.

Figure 8:
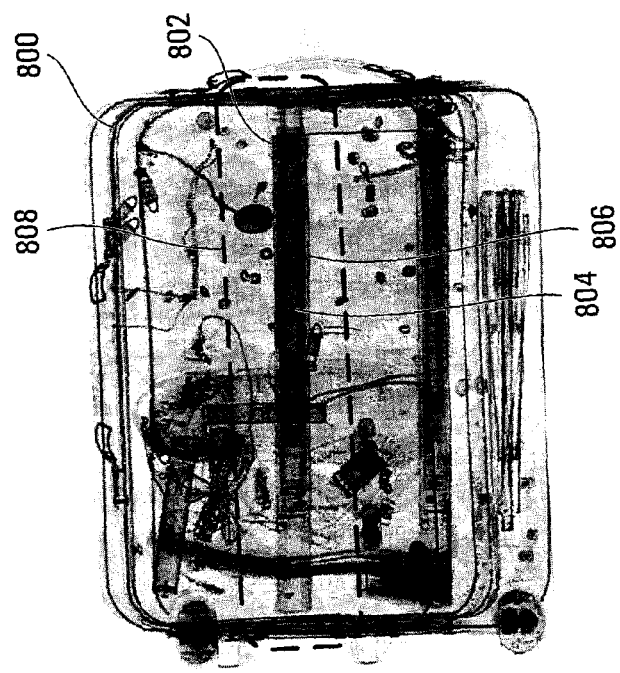
FIG. 8 is a more realistic X-ray image of a piece of luggage seen from the top.

FIG. 8 is representation of an X-ray image obtained with an X-ray scanner 350 shown in FIG. 2, namely a single view machine. The image shows a typical suitcase 800 and its contents. In order to clarify the image, either for the purpose of automatic threat detection or for producing a de-cluttered view for visual inspection by an operator, it is desirable to compensate the image such as to remove from it the X-ray signature of one or more objects in the suitcase 800. Some of the objects in the suitcase 800 are identifiable. Accordingly, it is possible to determine the contribution of those objects in the X-ray image and thus compensate the X-ray image accordingly.

(i) Determining Object Characterization Features Based on Shape.

The image processing operation that is performed tries to identify particular shapes in the X-ray image which can be associated with certain objects. Typical shapes or shape components that can be identified include:
1. straight edges that correspond to the border of an object;
2. curved edges;
3. edges meeting at an angle that correspond to an area of the object where two converging edges meet;
4. segments of circles;
5. complete geometric shapes such as circles, triangles, rectangles, ovals;

The software executed by the processing module 200 which performs the shape detection process applies the following logic:
1. The first step is to locate a portion of the edge of an object. The software searches the pixels of the X-ray image data for a detectable grey level transition that occurs in the image as a result of the presence of a sharp edge represented by a well defined grey level transition. To facilitate the edge detection process it is possible to provide the operator console 300 with user interface tools that will allow the operator to designate in the X-ray image the general area where the object to be removed from the X-ray image is located. In this fashion, the software will start the image analysis in an area of the image that is known to contain an object that can be removed. Specifically, the user interface on the console 300 is designed such as to display to the operator 130 the X-ray image obtained as a result of the scanning operation. Once the image is shown to the operator 130, he or she uses a tool to indicate where the object to be removed lies. FIG. 8 shows an example of such X-ray image where an object 802 in the form of an elongated rectangle appears. The object 802 is likely to be a metallic handlebar strip that is commonly used in suitcases to reinforce the suitcase structure.

The operator 130 first visually identifies the object that he/she wishes to remove from the image, which in this particular case is the object 802. The operator then uses a user interface tool to designate the object 802 to the software. The tool may be any suitable user interface tool such as pointer device such as a mouse or a touch sensitive feature allowing the operator 130 to touch the screen at the area of interest. When the pointer device is activated at the location 804, which by convention is deemed to correspond generally to the centre of the object 802, the activation will produce location data. The location data identifies an area in the image where the object 802 resides. The software uses the location data to select the portion of the image data to process. The software then scans the X-ray image data until a sharp grey level gradient is located that corresponds to an edge of the object 802.

Another possibility is for the operator to designate with the pointing device specifically the edge 806 of the object 802 that is to be removed. For instance the operator 130 "clicks" the mouse or touches the screen with his/her finger at the location 806 that corresponds to the edge of the object 802.

Yet another possibility is for the operator to perform the designation by "drawing" on the image a zone curtailing the area where the object 802 is located. For instance the operator 130 can use the pointing device to draw the line 808 (only a portion of the line shown for clarity) around the object 802.

With any one of the methods described earlier, the edge detection software receives operator guidance to perform an image analysis and extract from the image one or more characterizing features of the object 802.

Figure 23:
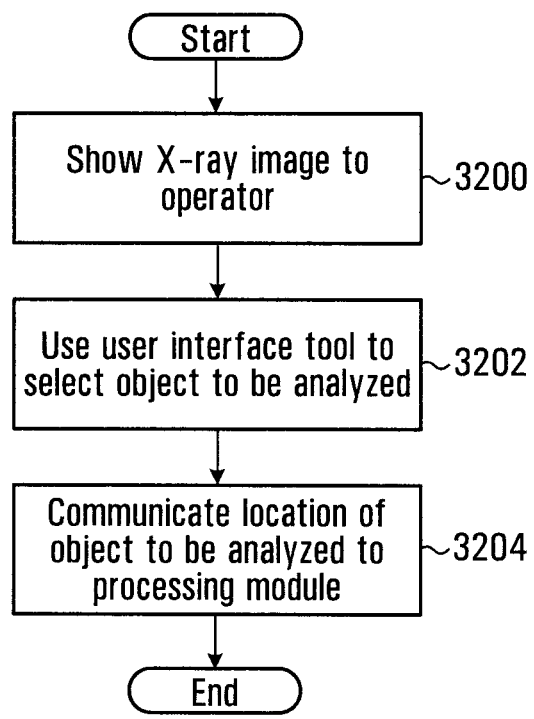
FIG. 23 is a flowchart of a process for allowing the operator to specify on the X-ray image at FIG. 8 a specific area of the image to be analyzed to determine the presence of object characterization features.

FIG. 23 provides a flowchart that summarizes the above process. At step 3200 the image of the luggage 104 is shown on the console 300 of the operator. At step 3202 the operator uses a suitable user interface tool to designate the area of the image to be processed. As indicated earlier, the user interface tool may be a pointing device, among others. At step 3204 information about the location in the image where area of interest resides is located is communicated to the processing module 200 such that the image analysis can be performed.

Referring back to FIG. 8, the next step of the process is to track the outline of the object 802. As the software has identified a portion of the object's edge, the software logic then starts tracking that edge. The tracking logic tracks the sharp grey level gradient in the image to follow the edge of the object 802.

2. When the tracking logic has completed the identification of the object edge, then the software can outline the object on the screen, as a final "sanity check". Specifically, the processing module 200 would issue commands to the display such that the display visually enhances a portion of the image where the object 802 is located. This makes the object more visible with relation to other objects in the X-ray image. Examples of image enhancements include:
  a. Colouring or otherwise highlighting the areas of the image that correspond to the portions where the edge has been identified;
  b. Colouring or otherwise highlighting the object in its entirety;
  c. De-emphasising the image except the areas where the object lies. This technique does not change the pixels of the X-ray image in the region of the object but changes all the pixels that surround the object image such as to make the object more visible.

The highlighting process uses the edge detection data obtained by the edge detection software as a result of the X-ray image analysis. The edge detection data defines in the X-ray image the areas where an edge has been identified. The highlighting process then uses this information to manipulate the X-ray image pixels such that the object stands out with relation to its surroundings.

If the edge identification has been done correctly the operator 130 would see the object 802 highlighted. The operator 130 can then apply human judgment on the results. If the edge tracking operation is correct then the results can be accepted and the processing allowed to continue. Otherwise, if the operator 130 sees on the screen a highlighted shape that does not correspond to a particular object in the image then he/she aborts the operation.

Note that it is not essential to rely on input by a human operator in order to perform the object detection analysis in the image. It is possible to process the entire X-ray image in order to pick up geometric shapes of objects therein. In this case, the amount of data that the processing module 200 will have to analyse is larger and the processing module 200 will need to be designed accordingly in order to perform the operation in an acceptable time frame.

(ii) Determining Object Characterization Features Based on Nature of Object Material.

The image processing operation that is performed identifies areas displaying relatively constant attenuation information which is indicative of an integral object. Once the area of constant attenuation information is identified the edge can be determined to obtain shape information. By relatively constant is meant that the X-ray attenuation information varies in a certain range.

(b) Determining Object Characterization Features in X-ray Data Conveying a Two or More Views of the Piece of Luggage.

The image processing operation to identify shapes or shape components as described earlier can be performed on each view separately and the results then subjected a further processing to identify the type of object that may be present in the suitcase. This further processing is described below.

3) Determine Type/Nature of Object

The information on the shape or shape components as well as the location of the shapes or shape components extracted during the previous processing operation are further processed to try determining what types of objects may be present in the image. One possibility is to use a rules engine that tries to match shapes or shapes components to object types that one is expected to find in a suitcase.

Figure 24:
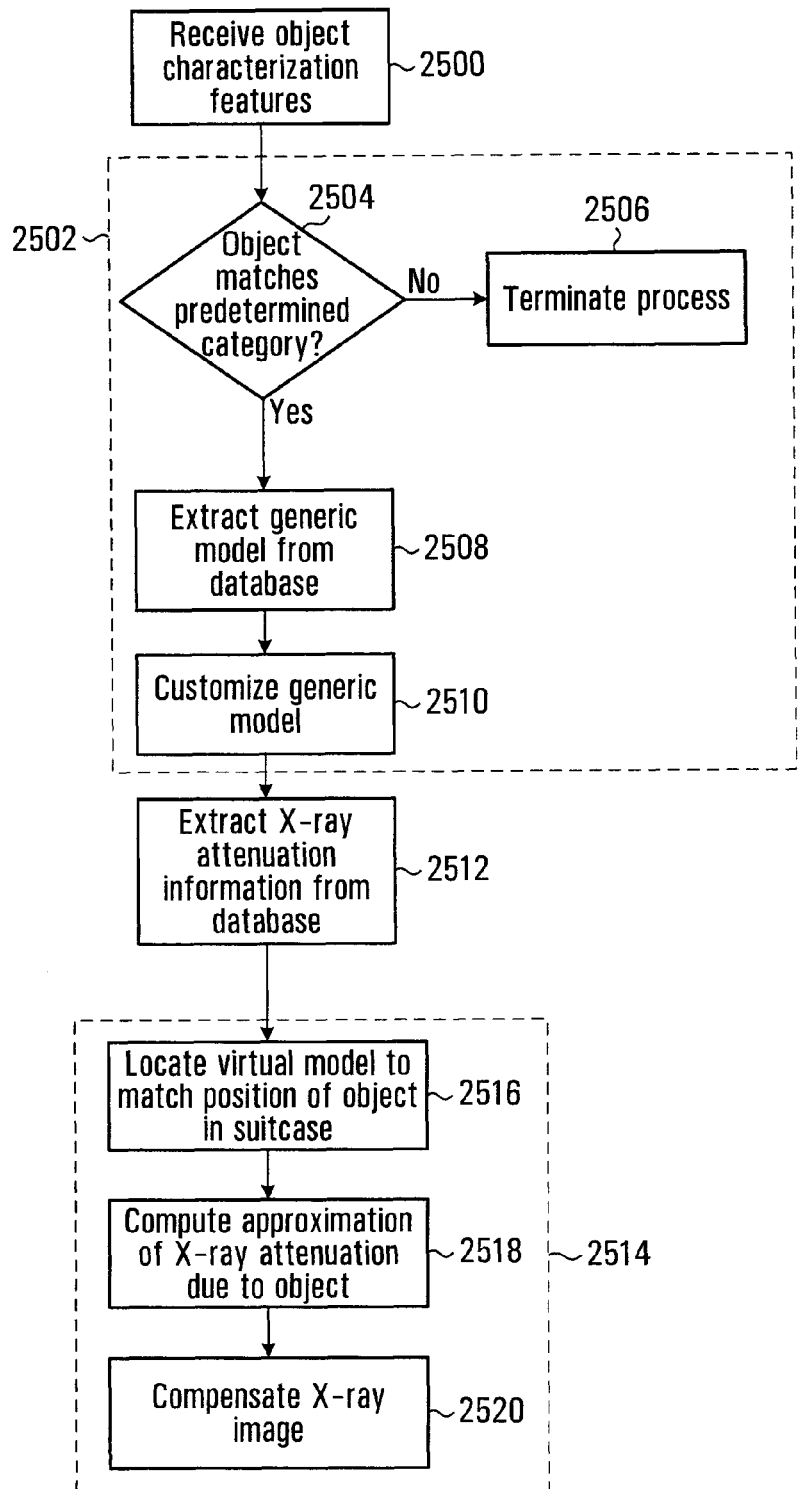
FIG. 24 is a flowchart of a process for modeling an object detected in an X-ray image to perform X-ray image data compensation.

This process is best illustrated in the flowchart of FIG. 24. Specifically, at step 2500 the data processing module 200 receives the object characterization features extracted during the previous processing step. The object characterization features include shapes or portions of shapes identified in the X-ray image and the location of those shapes in the image. During the processing, the shapes can be expressed in any convenient way, such as vector graphics, raster graphics or other.

When the X-ray image data conveys a single view of the suitcase 800, the processing is two dimensional, in the sense that the object determination operation will be done on the basis of an object shape/geometry from one point of view. In the case of multi view X-ray image data of the object, the processing takes into account object shape/geometries in three dimensions.

At step 2502, the processing module 200 generates a virtual model of the object. The generation of the virtual model is performed by the software executed by the processing module 200 which implements a series of logical rules. The rules use as an input characterization features or patterns to determine what the object likely is. The rules can be built in many different ways from simple logic designed to handle a limited number of object geometries or object types to a much more complex logic that can differentiate between many different object types and geometries.

For example, characterization features such as arcs can be assumed to indicate the presence of round objects, like coins in the suitcase or the suitcase wheels. Straight lines can indicate elongated rectangles such as the typical components used in the construction of the suitcase, such as the handlebars.

Therefore, the object characterization features appearing in the X-ray image constitute the basis on which the process determines what the object is. This process may operate by allocating the characterization features to a number of predetermined types of objects that may be commonly found in a suitcase. Some assumptions may be used to make conclusions as to the nature of the object. Those assumptions are implemented by a rules engine which processes the characterization features to try determining what type of object this might be. For example:

1. Disk like objects can be coins. Contextual information can be applied to validate the assumption. For example, it is known that coins cannot be larger than say 1.5 inches in diameter or smaller than 0.25 inches in diameter. Therefore, if the disc is in that range of diameters it might be a coin.
2. Elongated strip like objects that are shaped as rectangles and that extend across most of the X-ray image span are likely to be the telescoping handlebars most suitcases have. If more than one of the elongated strips is identified and all the strips are generally parallel, then the rules engine concludes that the suitcase has a pair of handle bars, in other words both strip-like objects belong to the handlebar.
3. Objects shaped as continuous looped filaments. When the object characterization data conveys an edge shape that is filament like and repeatedly loops, the rules engine concludes that the object is likely an electrical cord, such as a charging module for a laptop, cell phone, etc.
4. Laptop—a large generally rectangular outline that encompasses a series of other shapes, such as rectangles or circles can be indicative of a laptop. Laptops have a series of standardized components, such as disk drives that would appear circular, battery packs that would be generally of elongate rectangular shape and a series of rectangular small objects that would be the electronic chips on the board among others. In such case, when the rules engine makes the assumption that a laptop is present, on the basis of a collection of smaller shapes corresponding to the sub-components of the laptop computer can logically group the various components in one compound object that can then be manipulated electronically as a single entity.

When the X-ray image data conveys more than one view, such as two or three views of the suitcase 800, all those views can be used to build a three dimensional virtual model of the object. In the instance where location information is present, which identifies the position of an object characterization feature in a given view, it is possible to correlate object characterization features from several views to object geometry information about the object in three dimensions. Taking the example of the coins, if one view shows the object as a disk and another view shows the object as relatively thin strip, then the object is likely a coin. In addition to correlating the object characterization features from different views, multiple views also allow to "see" an object of interest from a perspective that makes it easier to identity. For example, an object in a suitcase may be oriented in such a way that it shows a confusing image in a particular view. Take the example of a small cosmetics bottle. When seen from the bottom, the bottle is likely to appear in the X-ray image as a disk-shaped article, suggesting a coin. From a different view however, the height dimension will appear significant, allowing resolving the ambiguity (the object is not a coin).

Accordingly, the processing performed on X-ray images that convey more than a single view of the suitcase is likely to yield better results.

The rules engine operating on single or multiple views X-ray images may use complex logic rules along with contextual information (such as for example if a laptop computer is assumed to be present, then a charging module should also appear somewhere in the image). Many different layers of logic can be integrated in the rules engine such that in addition to the object characterization features extracted from the X-ray image data, inferences can be made based on context to make reasonable assumptions as to what some objects might be. Non-limiting examples of contextual information can include:

1. Associated objects—the presence of one object indicates the presence of another object associated with it, such as:
    a. the presence of a laptop computer is also likely to reveal a charging module in the X-ray image;
    b. The presence of one shoe is likely to reveal in the X-ray image at least another shoe;
2. Type of suitcase—if the suitcase has at its periphery a pair of disk-like objects, which are likely to be rollers, handlebars are likely to be present too in the X-ray image. Accordingly, if elongated strip-like objects are identified in the X-ray image then those objects are likely to be handlebars in light of the presence of the rollers. On the other hand, if elongated strip-like objects are present but no rollers are found, the elongated strip-like objects may not be handlebars.

Sub-step 2504 in the flowchart in FIG. 24 illustrates the example discussed earlier, where the object is allocated to a predetermined object type based on object characterization features. The processing module 200 tries to allocate the object characterization features to an object type selected in a predetermined set of object types. The number of predetermined object types may vary depending on the specific application. The processing module may be designed to detect a single object type or multiple object types, without departing from the spirit of the invention. The allocation is performed by implementing the logic rules, as discussed earlier.

Sub-step 2504 is a conditional step which, if answered in the negative (no predetermined object type has been identified) terminates the process at step 2506. Otherwise, (a predetermined object type has been identified) leads to step 2508 at which a generic virtual model of the object is extracted from the database 28. The virtual model reflects in three dimensions the shape of the object. One possibility is to use a library of generic shapes stored in the database 28. For each type of object that the processing module 200 is capable to identify in the X-ray image on the basis of object characterization features, at least one generic virtual model is stored in the library of shapes. For instance, in the case of a laptop computer, the virtual model would be rectangular block.

The generic virtual model is then customized by the processing module 200, at step 2510 to fit the shape observed in the image. This is done by re-sizing the generic model such as to produce a model that more closely matches the object as seen in the X-ray image. The re-sizing can be done according to the information that is available on the object in the X-ray image. In the case of a single view image, dimensional information on the object may be available on two axes. In a multi view scenario, dimensions of the three axes may be available. For example, in the case of a laptop in the luggage, the object characterization features could allow determining the length and width dimensions of the laptop, thus allowing resizing the generic model along those two axes. If the X-ray image is a single view image, where no height dimension is available, then only a two dimension resizing is made and the adapted virtual model retains the height dimension of the generic virtual model. In the case of multi-view X-ray image data, then the resizing may be made on all three axes.

Once the type of object is determined and its virtual model generated, its material properties are assessed at step 2512. This operation may also involve the database 28. Specifically, the database 28 maps the type of objects with and indicator that can be used to compute the degree of X-ray attenuation the object will manifest. Accordingly, when the rules engine has identified the type object that exists in the X-ray image, it performs an interaction with the database 28 in order to determine what the indicator is. Note that in most applications the indicator does not need to be extremely precise and may be such as to compute an approximate degree of X-ray attenuation for the object.

For example, in the case of a laptop computer the indicator can be such that the computed attenuation value will be average for a typical laptop computer. The indicator may not be constant or the same for the entire object and may be expressed as a pattern, where the attenuation is not constant across the object. A pattern, in the case of a roller of a suitcase, would provide a certain attenuation value for the periphery of the roller and a different attenuation value for the center, to account for the presence of the bearing which is likely to absorb more X-rays due to the presence of metallic material.

Similarly, in the case of a laptop computer, the indicator could specify more attenuation in areas of the machine where more dense components are located, hence were more X-ray absorption takes place. Yet another possibility for a laptop computer, instead of treating the machine as a single unit, it is possible, once the presence of a laptop computer has been identified in the image, to consider different components of the laptop computer and allocate to the different components respective indicators. For example, a laptop computer is likely to have a series of components such as a battery, hard drive, keyboard and electronics board. The presence of each component in the image can be identified and an indicator associated to it independently of another component.

Accordingly, the database 28 is organized such as to map different objects to an indicator from which can be derived X-ray attenuation information.

One specific example of indicator is density information for the object. Since density determines to a significant extent the X-ray absorption, density information can be used to compute the X-ray attenuation due to the object. As indicated previously, the density information associated with a certain object may be a constant value, or may convey a density pattern assigning producing different attenuation levels to different parts of the object. Another example of an indicator is a value that provides a direct indication of the amount or degree of X-ray attenuation the object provides per unit volume.

4) Remove Contribution of Object in X-Ray Image Data

The purpose of this step, illustrated at FIG. 24 as 2514 is to compensate the X-ray image data such as to remove partially or completely the X-ray signature of the object into the image. Conceptually, this results into a full or complete removal of the visual signature of an object or a component thereof in the image, making the image clearer and therefore facilitating threat processing either automatic or performed by a human operator.

The first sub-step 2516 is to manipulate virtual model such as to correctly locate that virtual model in the suitcase environment. More specifically, the processing module 200 performs rotations of the virtual model or translations of the virtual model such that it matches the position of the real object in the suitcase. The manipulations on the virtual model are made with relation to the characterizing features seen in the X-ray image. Generally, the processing module would manipulate the virtual model in three dimensions such that it would appear to an observer that looks at the suitcase from the point of view of the X-ray source, to overlay the object shown in the X-ray image.

This operation may require constructing a virtual model of the entire scanning area of the X-ray scanner in which a virtual model of the suitcase is also created. The virtual model of the scanning area usually would need to be generated once and can be re-used for subsequent scanning cycles since the X-ray scanner 100 does not change, hence the virtual model would be also static. The model includes the three dimensional position of a number of different components, such as:
  The three-dimensional position of the X-ray source. For simplicity, the X-ray source can be expressed in the model as a single point characterized by a set of three-dimensional coordinates;
  The position of the various detectors, each detector described as a single point entity characterized by a set of three dimensional coordinates;
  The position of the belt, described as a surface;

Once the orientation of the virtual model of the object relative to the virtual model of the scanning area is determined, it is possible to compute an approximation of the attenuation that the object would manifest in the image (sub-step 2518). Since the a priori X-ray attenuation information is available from the database 28, it is possible to compute the attenuation the object would manifest given its orientation. The degree of X-ray attenuation is determined largely by the nature of the material and the so called "path length" which is the thickness of the material through which the X-rays travel. The path length is a factor that depends on the orientation of the object in the scanning area. An object that is thin and flat will attenuate the X-rays differently, depending upon its position with respect to the X-ray source. If the object is located such that it is generally perpendicular to the direction according to which the X-ray source generates X-rays, the thickness of the material that the X-rays pass through is small by comparison to another orientation in which the X-rays travel through the object in a direction parallel to the plane of the object.

An example of scanning area modelisation is described in the Canadian patent application 2,696,031, filed on 2009-06-09 and entitled "Method and system for performing X-ray inspection of a product at a security checkpoint using simulation". The contents of this patent application are hereby incorporated by reference.

However, in light of the fact that the orientation of the virtual model in the scanning area has been established such as to mach the orientation of the real object, to the processing module 200 geometrically computes the path length through the virtual model at different locations on the object. For example, in the case of any object, the path length will be the distance separating two interception points between an imaginary straight line along which an X-ray travels and the boundary of the object. Essentially, the first interception point is the point at which the X-ray enters the virtual model. The second interception point is the point at which the X-ray exits the virtual model. The distance between those points is the path length for that particular X-ray.

The above process can be repeated a number of times to compute the path length at different areas of the object such as to more precisely determine the X-ray attenuation pattern obtained in light of the particular object orientation.

In this example, the processing module uses a priori information about interaction between X-rays and the object, available in the database 28. The resulting X-ray attenuation information that is generated is synthetic information in the sense that it is not extracted directly from the image, rather it is computed by simulating how the object would interact with X-rays.

The removal of the X-ray attenuation that the real object manifests in the image is done by compensating the X-ray image data by using the synthetic attenuation information computed earlier. This is shown at step 2520. Assuming that the X-ray image data expresses attenuation information as gray levels, the compensation can be done by modifying the grey levels of the in the boundary of the object according to the attenuation pattern computed earlier in order to produce a compensated image that will show a lesser degree of attenuation within that boundary. Specifically, the compensation includes computing new attenuation values for each pixel within the boundary of the object, where the new attenuation value is the difference between the attenuation value of the original pixel reduced by the computed attenuation value caused by the object at that pixel location. The result of this operation is a compensated X-ray image in which the object has been "erased". A complete erasure would occur if the computed attenuation matches precisely the real X-ray signature in the X-ray image data. While this is a desired objective, in most cases it is not necessary to fully "erase" an object. It may be sufficient to compensate the image up to an extent that other objects, previously obscured, are now sufficiently detailed allowing performing an adequate threat assessment of the suitcase.

Accordingly, applications of the invention are possible in which it is not necessary to implement the path length computation described earlier. It may suffice to assign to the virtual model a constant attenuation value, irrespective of its orientation, such as to compensate the X-ray image data to some extent and thus improve its clarity. In this example, the pixels within the boundary of the object will be compensated uniformly.

FIGS. 10 to 13 illustrate a specific example of implementation where an X-ray image of a suitcase is processed to obtain a compensated X-ray image in which the handlebars are effectively removed from the image.

Figure 10:
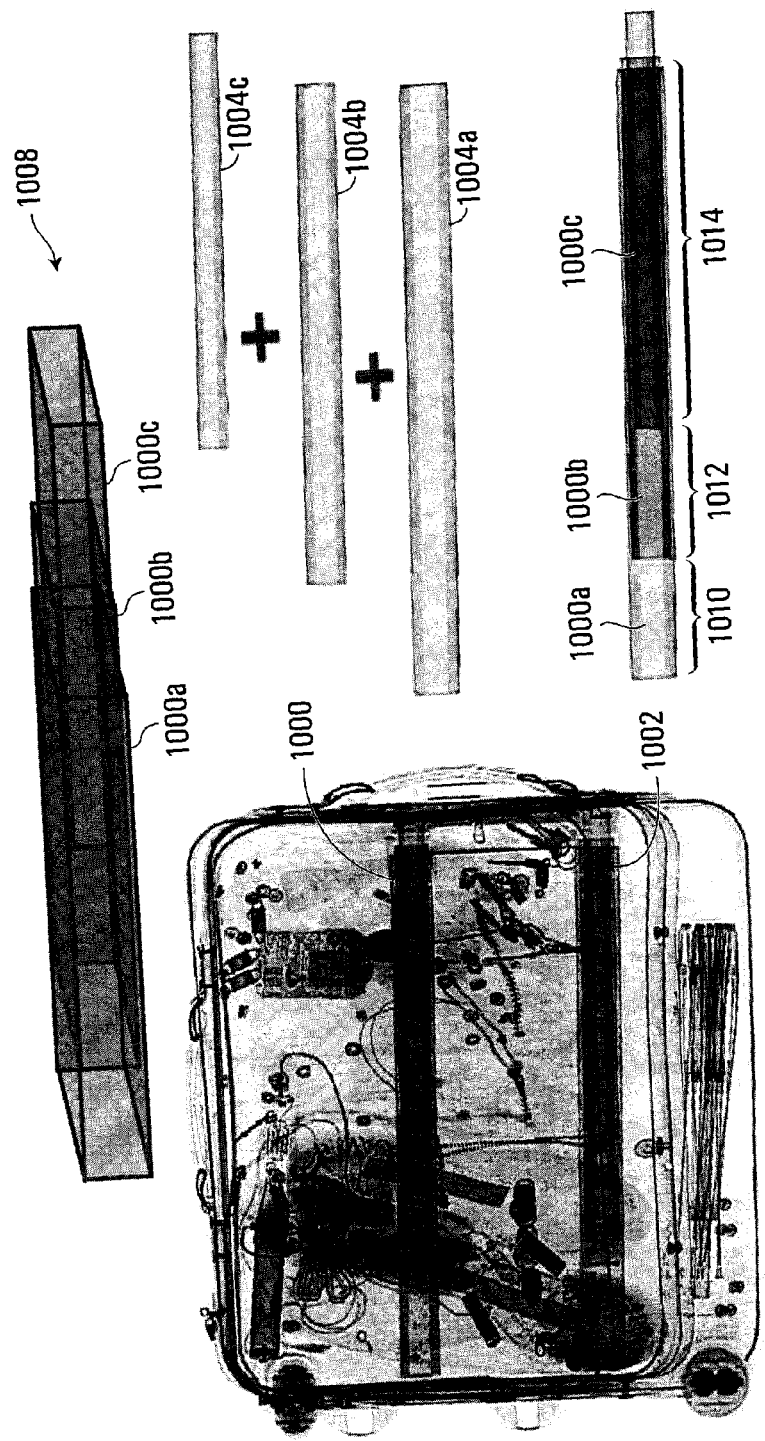
FIG. 10 is an X-ray image of a piece of luggage seen from the top, also showing how the X-ray signatures of objects that overlay one another form the X-ray image.

In FIG. 10, the X-ray image of the suitcase shows clearly two handlebars 1000 and 1002 that are clearly visible as two generally parallel elongated rectangular strips. The processing of the X-ray image data is performed and the processing identifies the objects as the handlebars.

More specifically, the handlebars are composite structures, which appear in the X-ray image as nested rectangles, namely 1000*a*, 1000*b* and 1000*c*, where each rectangle is associated with a telescoping part of the handlebar. The handlebar 1002 is constructed in a similar fashion. The detection process as discussed earlier identifies each handlebar component separately and builds for each component an associated virtual model. The virtual models 1004*a*, 1004*b* and 1004*c* are associated with the components 1000*a*, 1000*b* and 1000*c*, respectively. The virtual models 1004*a*, 1004*b* and 1004*c* are then manipulated by the processing entity 200 such as to locate them one relative to the other as per the positioning of the original objects 1000*a*, 1000*b* and 1000*c*. The result of the manipulation of the virtual models 1004*a*, 1004*b* and 1004*c* is shown at 1008, where the models are nested according to the position of the original objects 1000*a*, 1000*b* and 1000*c* in the suitcase.

Figure 13:
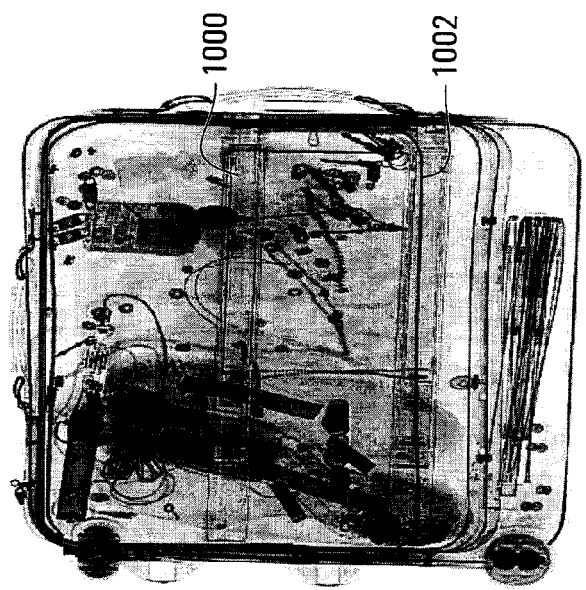
FIG. 13 shows the X-ray image of FIG. 11, compensated to remove the contribution of the handle bars in the image.
Figure 12:
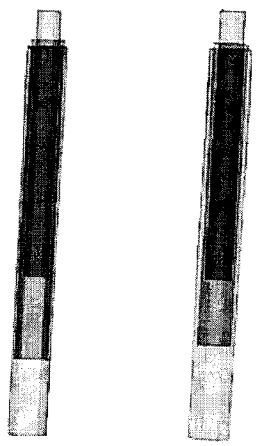
FIG. 12 is representation of a computer generated model of the X-ray signature of the handle bars.
Figure 11:
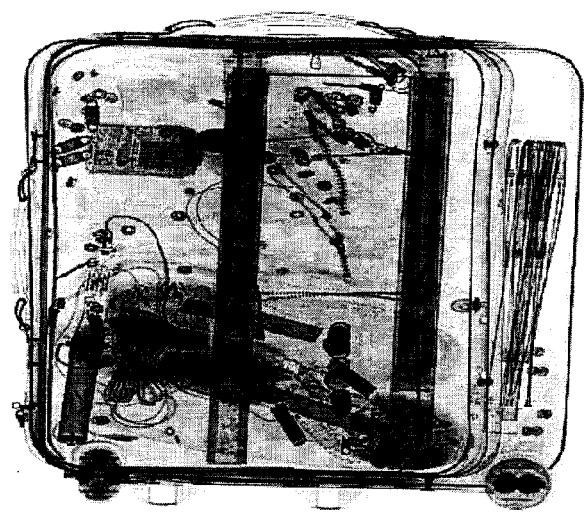
FIG. 11 is an X-ray image of a piece of luggage seen from the top, the image containing the X-ray signatures of a pair of handle bars.

FIG. 13 illustrates the compensated X-ray image in which the handlebars 1000 and 1002 are almost no longer visible. The image compensation is such, however that other objects in the image that were overlapping with the handlebars, are now more clearly visible.

In this example, the X-ray image compensation process is such that the computed degree of attenuation associated with a handlebar 1000, 1002 is not uniform, rather it varies to take into account the increased attenuation due to the telescoping arrangement of the components 1000*a*, 1000*b* and 1000*c*. In this instance a first degree of attenuation is associated to the portion 1010, a second higher degree of attenuation is associated to the portion 1012 and a third even higher degree of attenuation is associated with the portion 1004 where the three components overlap. The virtual model of the handlebar takes into account the compounding X-ray attenuation effect due to the various components of the model. According to this arrangement, the zone of the X-ray image that is associated with the portion 1010 is compensated to a first degree, the zone of the image that is associated with the portion 1012 is compensated to a second higher degree and the zone of the image that is associated with the portion 1014 is compensated to a third yet higher degree. This example illustrates the possibility of providing virtual models of objects that are not merely made of uniform blocks, but represent the object by modeling independently respective components. In this situation, the handlebar is represented by a virtual model that has individual components which can be manipulated independently of one another by the processing module 200.

Figure 16:
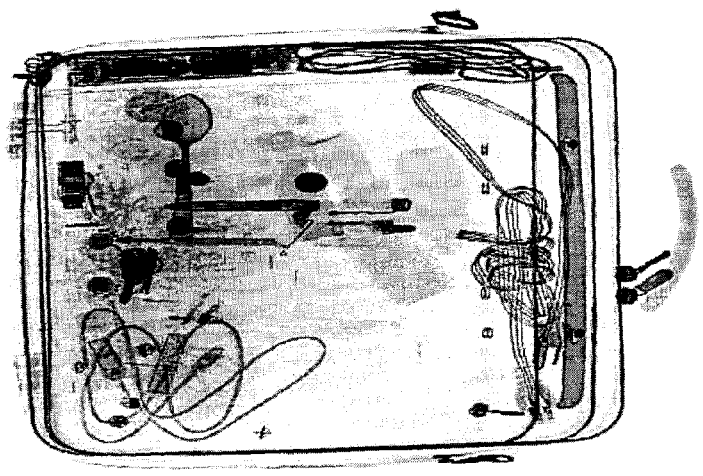
FIG. 16 shows the X-ray image of FIG. 14, compensated to remove the contribution of the laptop computer in its entirety.
Figure 15:
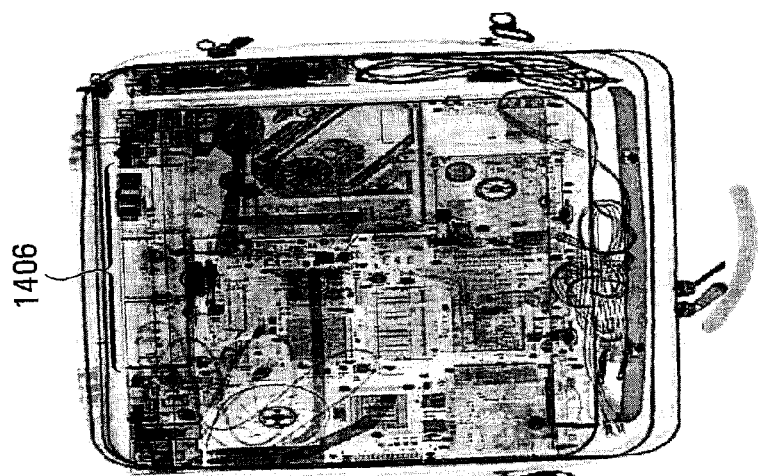
FIG. 15 shows the X-ray image of FIG. 14, compensated to remove the contribution of some components of the laptop computer.
Figure 14:
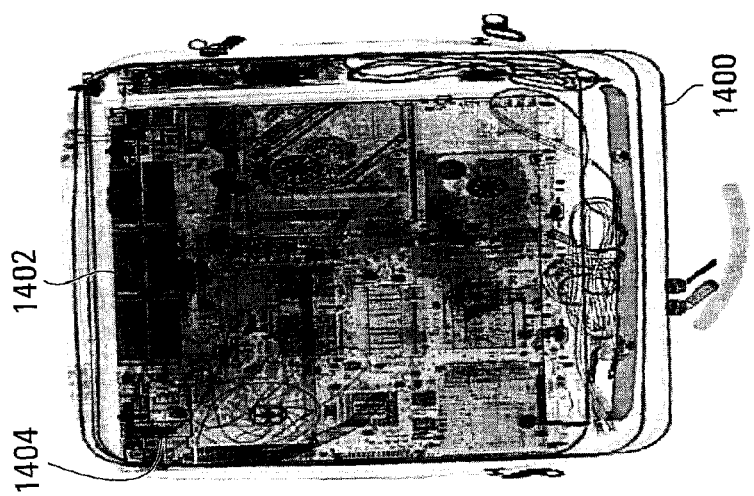
FIG. 14 is an X-ray image of a piece of luggage seen from the top, the image illustrating the X-ray signature of a laptop computer.

Yet another example of implementation is shown at FIGS. 14, 15 and 16. In this example, a suitcase 1400 is scanned with the X-ray scanner 100 which produces the X-ray data rendering the image at FIG. 14. The suitcase 1400 contains a laptop computer 1402. The image is processes as discussed earlier in order to "remove" as much as possible the laptop computer 1402. The removal proceeds in phases. The processing identifies individual components of the laptop computer 1402, on the basis of their shape, and compensates the X-ray image data accordingly. A first compensation yields the compensated image shown at FIG. 15. In that image, a component 1404 of the laptop computer which can be the battery thereof or a bank of computer chips has been identified as such and almost completely "erased" from the image. The reference numeral 1406 in FIG. 15 identifies the location of the component 1404 and shows other elements, overlapping in the suitcase with the component 1404, much more clearly visible in the compensated image. FIG. 16 shows a further compensated X-ray image in which the laptop computer is no longer visible.

A significant advantage of this example is the ability to process luggage that contains electronic devices such as laptop computers, cell phones without the necessity to remove the electronic devices from the luggage. A person carrying such luggage at a security checkpoint would therefore simply put the luggage on the conveyor belt such that the luggage is scanned. The resulting X-ray image is processed as described earlier, with compensation implemented progressively until the clarity of the image improves to the point the operator is confident that the suitcase does not contain prohibited objects.

One example of a prohibited object which can be more easily detected with the present invention is sheet explosives.

Explosive materials can be formed as thin sheets and those can be integrated in electronic devices, such as laptop computers. The ability of the present method to "remove" from the X-ray image components of the laptop computer that are known and expected to be found, would therefore leave the sheet explosive visible.

Figure 25:
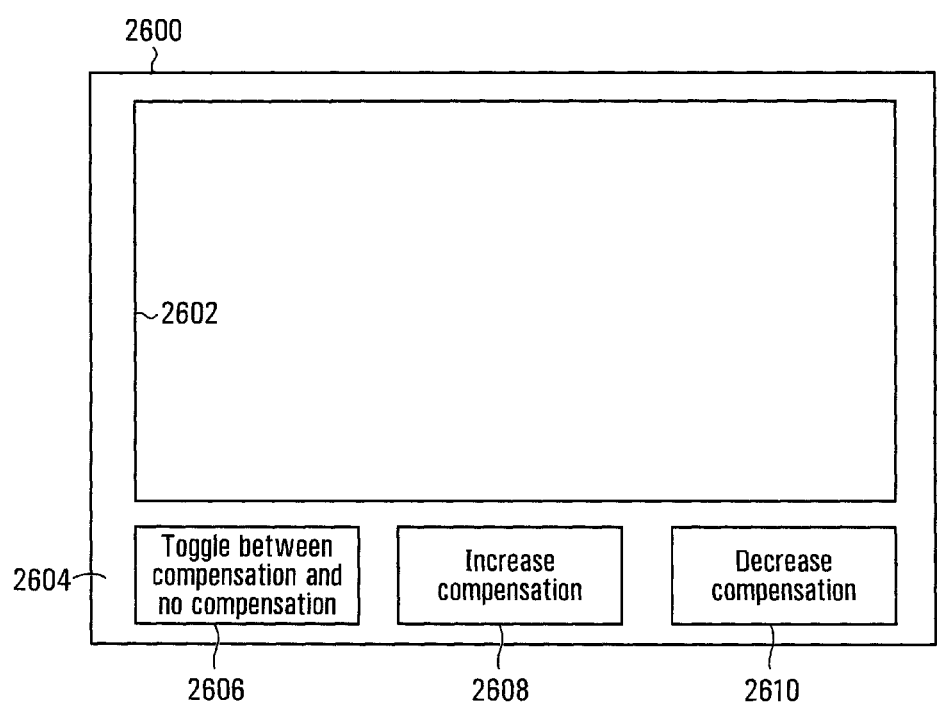
FIG. 25 is an image of a display screen showing Graphical User Interface tools (GUI) that can assist the operator to control the display of the X-ray image of the luggage and accordingly, the visual inspection of the contents of the luggage.

FIG. 25 is a block diagram of a user interface that allows the operator to control the X-ray image compensation process performed by the processing module 200 and how the compensated X-ray image is presented. The user interface is preferably a GUI (Graphical User Interface) that provides the operator with controls allowing communicating with the processing module 200 in order to control the X-ray image compensation process such as to fine tune it in a way that better suits the preferences of the operator.

FIG. 25 illustrates the display associated with X-ray scanner 10 and could be integrated with the console 300 or at the security station 500. The display 2600 is connected to the processing module 200 to receive the X-ray image signal for display in a display area 2602. In use, the display area would be displaying the X-ray images of the luggage that is scanned by the X-ray scanner 10. Below the display area 2602 is provided a control area 2604 in which are provided a series of GUI tools allowing the operator to issue commands to the processing module 200. In the example shown, the GUI tools are operated by touch, in other words, the operator touches virtual buttons on the screen. The touch is detected by the display device 2600 and a control signal is sent to the processing module 200. Alternatively, the GUI tools can be operated via a pointing device, or voice recognition. Another possibility is to use tools that are independent of the display 2600, such as dedicated keys on a keyboard.

In the specific example shown, the user interface tools provide three types of functions. A first virtual button 2606 is provided to allow the operator to toggle the X-ray image between a compensated and a non-compensated view. The non-compensated view would be the original X-ray view in which the attenuation information due to the object is present. The compensated view is derived from the processing of the X-ray image information to produce an X-ray image from which some of all of the attenuation information due to the object has been removed. The toggle function may be useful for the operator to determine which image is best to assess if the suitcase contains dangerous items. Since the X-ray compensation process removes information from the image, circumstances may arise when the resulting image is not clearer or more desirable than the original image. Thus, by toggling between the two images, the operator may determine which one is best for the visual threat assessment process.

To toggle the X-ray image in response to the actuation of the tool 2606, the processing module 200 keeps in the memory 302 X-ray image data of each representation (non-compensated and compensated) and sends image signals according to what the operator wants to see, as indicated by the tool 2606.

A second virtual button 2608 is provided to increase the degree of X-ray compensation in the image. This may be useful in instances where the operator sees that the degree of X-ray compensation is not enough and more compensation would be desirable to further remove or diminish the visual presence of the object in the image. The processing module responds to a control signal received from the display 2600 by re-processing the X-ray image, this time applying more compensation within the boundaries of the object. One specific possibility is to run the compensation process but modifying the X-ray attenuation indicator associated with the object, such that a higher degree of X-ray attenuation is attributed to the object. The tool may be designed such that each time the virtual button 2608 is pressed, an incremental compensation run is performed by the processing module 200, to add an additional level of compensation. In this fashion, when the X-ray image appears in the display area 2602, it is provided with a base level of compensation and the operator increases the compensation incrementally by pressing on the virtual button 2608 the desired number of times to make the image as clear as possible for the visual threat examination.

The third virtual button 2610 is the reverse of the virtual button 2608 in that it decreases incrementally the X-ray compensation in the image in the boundary of the object.

Another possible tool which may be provided to the operator is a depiction of the boundary of the object in the image in the display area 2602. This boundary can be presented in colors or in a manner to make it more visually distinct from other articles in the image and it is useful to show the operator where the object on the basis of which the compensation was made, resides in relation the remainder of the suitcase contents. This operation is performed by the processing module 200 on the basis of the virtual model of the object generated during the X-compensation operation. The processing module 200 performs additional processing that superposes the outline of the virtual model over the characterizing features of the object appearing in the X-ray image to produce a composite image that is then shown in the display area 2602. This provides the operator with the ability to visually determine if the object removal operation from the image is sound. If the boundary depicted in the image does not make sense, indicating that the processing module 200 has performed an erroneous operation, then the operator can toggle via the virtual button 2606 to the non-compensated view to perform the visual threat assessment operation.

Although various embodiments have been illustrated, this was for the purpose of describing, but not limiting, the invention. Various modifications will become apparent to those skilled in the art and are within the scope of this invention, which is defined more particularly by the attached claims.

The invention claimed is:

1. A method for assessing a threat status of a piece of luggage, said method comprising:
   a) receiving X-ray image data derived by scanning the piece of luggage with a scanning device using X-rays, the X-ray image data conveying information about an attenuation of X-rays resulting from X-rays travelling through the piece of luggage;
   b) processing the X-ray image data with a computing device programmed with software for:
      i) detecting an object in the piece of luggage;
      ii) deriving an X-ray signature associated with the detected object, the derived X-ray signature associated with the detected object conveying an amount of X-ray attenuation attributed to the detected object, wherein the X-ray signature associated with the detected object is derived at least in part by processing a virtual model of the detected object to simulate interactions between the detected object and X-rays;
      iii) deriving compensated X-ray image data at least in part by reducing in the X-ray image data effects of object induced X-ray attenuation resulting from X-rays travelling through the detected object based at least in part on the derived X-ray signature associated with the detected object;
      iv) determining the threat status of the piece of luggage at least in part based on the compensated X-ray image data.

2. A method as defined in claim 1, wherein deriving the compensated X-ray image data includes extracting a priori information from a knowledge database about interactions between X-rays and the detected object.

3. A method as defined in claim 2, wherein deriving the compensated X-ray image data includes deriving the X-ray signature associated with the detected object at least in part based on the a priori information.

4. A method as defined in claim 1, wherein simulating interactions between the detected object and X-rays includes generating the virtual model of the object.

5. A method as defined in claim 1, wherein detecting the object in the piece of luggage includes processing the X-ray image data to identify object characterization features.

6. A method as defined in claim 1, wherein detecting the object in the piece of luggage includes processing a user input signal conveying a location corresponding to the object in an image of the piece of luggage derived based on the X-ray image data.

7. A method as defined in claim 6, wherein said method comprises:
   a) processing the X-ray image data to render the image of the piece of luggage on a display device;
   b) providing a control for allowing a user to select the location corresponding to the object on the rendered image of the piece of luggage.

8. A method as defined in claim 1, wherein deriving the compensated X-ray image data includes:
   a) identifying a portion of the X-ray image data corresponding to the detected object;
   b) reducing in the identified portion of the X-ray image data effects of object induced X-ray attenuation resulting from X-rays travelling through the detected object based at least in part on the derived X-ray signature associated with the detected object.

9. A method as defined in claim 1, wherein determining the threat status of the piece of luggage includes processing the compensated X-ray image data to render an image of the piece of luggage on a display to assist an operator in determining if the piece of luggage contains prohibited objects.

10. A method as defined in claim 9, comprising providing a user activated control for transmitting command signals to the computing device, the computing device being responsive to the command signals to alter a degree to which the effects of object induced X-ray attenuation are reduced in the X-ray image data.

11. A method as defined in claim 9, wherein the image of the piece of luggage rendered on the display device includes an overlay image conveying a position of the detected object.

12. A method as defined in claim 1, wherein determining the threat status of the piece of luggage includes processing the compensated X-ray image data with an automated threat detection engine to determine if the piece of luggage contains prohibited objects.

13. A method as defined in claim 1, wherein the detected object includes a laptop computer.

14. A method as defined in claim 1, wherein the detected object includes an electronic device.

15. A method as defined in claim 1, wherein the detected object includes a handle bar.

16. A system for assessing a threat status of a piece of luggage, comprising:
   a) an X-ray scanner for scanning the piece of luggage with X-rays to derive X-ray image data, the X-ray data conveying information about an attenuation of X-rays resulting from X-rays travelling through the piece of luggage;
   b) a computing system including at least one processor, the computing system being in communication with said X-ray scanner and being programmed with software for:
      i) processing the X-ray image data to detect an object in the piece of luggage;
      ii) deriving an X-ray signature associated with the detected object, the derived X-ray signature associated with the detected object conveying an amount of X-ray attenuation attributed to the detected object, wherein the X-ray signature associated with the detected object is derived at least in part by processing a virtual model of the detected object to simulate interactions between the detected object and X-rays;
      iii) processing the X-ray image data to derive compensated X-ray image data at least in part by reducing in the X-ray image data effects of object induced X-ray attenuation resulting from X-rays travelling through the detected object, the compensated X-ray image data being derived at least in part based on the derived X-ray signature associated with the detected object;
      iv) deriving information for use in determining the threat status of the piece of luggage at least in part by processing the compensated X-ray image data;
   c) a display module in communication with said computing system for conveying information derived by said at least one processor.

17. An apparatus for assessing a threat status of a piece of luggage, the apparatus comprising:
   a) an input for received X-ray image data derived by scanning the piece of luggage with an X-ray scanner, the X-ray data conveying information about an attenuation of X-rays resulting from X-rays travelling through the piece of luggage;
   b) a computing device including at least one processor, said computing device being in communication with said input and being programmed for:
      i) processing the X-ray image data to detect an object in the piece of luggage;
      ii) deriving an X-ray signature associated with the detected object, the derived X-ray signature associated with the detected object conveying an amount of X-ray attenuation attributed to the detected object, wherein the X-ray signature associated with the detected object is derived at least in part by processing a virtual model of the detected object to simulate interactions between the detected object and X-rays;
      iii) processing the X-ray image data to derive compensated X-ray image data at least in part by reducing in the X-ray image data effects of object induced X-ray attenuation resulting from X-rays travelling through the detected object, the compensated X-ray image data being derived at least in part based on the derived X-ray signature associated with the detected object;
      iv) deriving information for use in determining the threat status of the piece of luggage at least in part by processing the compensated X-ray image data;
   c) an output for releasing data conveying results obtained by the computing device.

18. A non-transitory computer readable storage medium storing a program element for execution by a computing device for assessing a threat status of a piece of luggage, the program element, when executed by the computing device, causing the execution of a method by the computing device comprising:
   i) receiving X-ray image data derived by scanning the piece of luggage with a scanning device using X-rays, the X-ray image data conveying information about an attenuation of X-rays resulting from X-rays travelling through the piece of luggage;

ii) processing the X-ray image data to detect an object in the piece of luggage;

iii) deriving an X-ray signature associated with the detected object, the derived X-ray signature associated with the detected object conveying, an amount of X-ray attenuation attributed to the detected object, wherein the X-ray signature associated with the detected object is derived at least in part by processing a virtual model of the detected object to simulate interactions between the detected object and X-rays;

iv) processing the X-ray image data to derive compensated X-ray image data at least in part by reducing in the X-ray image data effects of object induced X-ray attenuation resulting from X-rays travelling through the detected object, the compensated X-ray image data being derived at least in part based on the derived X-ray signature associated with the detected object;

v) deriving information for use in determining the threat status of the piece of luggage at least in part by processing the compensated X-ray image data.

19. A method for assessing a threat status of a piece of luggage, said method comprising:

a) processing an X-ray image of the piece of luggage to detect a depiction of an object held in the piece of luggage;

b) deriving an X-ray signature associated with the object whose depiction was detected in the X-ray image of the piece of luggage, the X-ray signature conveying an amount of X-ray attenuation attributed to X-rays travelling through the object, wherein the amount of X-ray attenuation attributed to X-rays travelling through the object is derived at least in part by processing a virtual model of the object to simulate interactions between the object and X-rays;

c) processing the X-ray image to derive a compensated X-ray image of the piece of luggage by removing from the X-ray image at least part of the depiction of the object, the compensated X-ray image data being derived at least in part by compensating the X-ray image based on the derived amount of X-ray attenuation attributed to X-rays travelling through the object whose depiction was detected;

d) determining the threat status of the piece of luggage at least in part based on the compensated X-ray image of the piece of luggage.

20. A method as defined in claim 19, wherein determining the threat status of the piece of luggage includes rendering the compensated X-ray image of the piece of luggage on a display to assist an operator in determining if the piece of luggage contains prohibited objects.

21. A method as defined in claim 19, wherein determining the threat status of the piece of luggage includes processing the compensated X-ray image of the piece of luggage with an automated threat detection engine to determine if the piece of luggage contains prohibited objects.

22. A method as defined in claim 19, wherein removing from the X-ray image at least part of the depiction of the object includes generating the virtual model of the object.

23. A method as defined in claim 19, wherein the object includes a laptop computer.

24. A method as defined in claim 19, wherein the object whose depiction was detected in the X-ray image of the piece of luggage includes an electronic device.

25. A method as defined in claim 19, wherein the object whose depiction was detected in the X-ray image of the piece of luggage includes a handle bar.

26. A system for assessing a threat status of a piece of luggage, the system comprising:

a) an X-ray scanner for scanning the piece of luggage with X-rays to derive an X-ray image of the piece of luggage, the X-ray image of the piece of luggage conveying information about an attenuation of X-rays resulting from X-rays travelling through the piece of luggage;

b) a computing system including at least one processor, said computing system being in communication with said X-ray scanner and being programmed with software for:

i) processing the X-ray image of the piece of luggage to detect a depiction of an object held in the piece of luggage;

ii) deriving an X-ray signature associated with the object whose depiction was detected in the X-ray image of the piece of luggage, the X-ray signature conveying an amount of X-ray attenuation attributed to X-rays travelling through the object, wherein the amount of X-ray attenuation attributed to X-rays travelling through the object is derived at least in part by processing a virtual model of the object to simulate interactions between the object and X-rays;

iii) processing the X-ray image of the piece of luggage to derive a compensated X-ray image of the piece of luggage by removing from the X-ray image of the piece of luggage at least part of the depiction of the object, the compensated X-ray image data being derived at least in part by compensating the X-ray image based on the derived amount of X-ray attenuation attributed to X-rays travelling through the object whose depiction was detected;

iv) deriving information for use in determining the threat status of the piece of luggage at least in part by processing the compensated X-ray image of the piece of luggage;

c) an output for releasing data conveying results obtained by the computing system.

27. A non-transitory computer readable storage medium storing a program element for execution by a computing device for assessing a threat status of a piece of luggage, the program element, when executed by the computing device, causing the execution of a method by the computing device comprising:

a) processing an X-ray image of the piece of luggage to detect a depiction of an object held in the piece of luggage;

b) deriving an X-ray signature associated with the object whose depiction was detected in the X-ray image of the piece of luggage, the X-ray signature conveying an amount of X-ray attenuation attributed to X-rays travelling through the object, wherein the amount of X-ray attenuation attributed to X-rays travelling through the object is derived at least in part by processing a virtual model of the object to simulate interactions between the object and X-rays;

c) processing the X-ray image to derive a compensated X-ray image of the piece of luggage by removing from the X-ray image at least part of the depiction of the object, the compensated X-ray image data being derived at least in part by compensating the X-ray image based on the derived amount of X-ray attenuation attributed to X-rays travelling through the object whose depiction was detected;

d) deriving information for use in determining the threat status of the piece of luggage at least in part by processing the compensated X-ray image of the piece of luggage.

28. A system as defined in claim 16, wherein simulating interactions between the detected object and X-rays includes generating the virtual model of the object.

29. A system as defined in claim 16, wherein detecting the object in the piece of luggage includes processing the X-ray image data to identify object characterization features.

30. A system as defined in claim 16, wherein detecting the object in the piece of luggage includes processing a user input signal conveying a location corresponding to the object in an image of the piece of luggage derived based on the X-ray image data.

31. A system as defined in claim 16, wherein the computing system is programmed with software for:
   a) processing the X-ray image data to render the image of the piece of luggage on a display device;
   b) providing a control for allowing a user to select the location corresponding to the object on the rendered image of the piece of luggage.

32. A system as defined in claim 16, wherein deriving the compensated X-ray image data includes:
   a) identifying a portion of the X-ray image data corresponding to the detected object;
   b) reducing in the identified portion of the X-ray image data effects of object induced X-ray attenuation resulting from X-rays travelling through the detected object based at least in part on the derived X-ray signature associated with the detected object.

33. A system as defined in claim 16, wherein determining the threat status of the piece of luggage includes processing the compensated X-ray image data to render an image of the piece of luggage on a display to assist an operator in determining if the piece of luggage contains prohibited objects.

34. A system as defined in claim 33, wherein the computing system is programmed with software for providing a user activated control for transmitting command signals to the computing device, the computing device being responsive to the command signals to alter a degree to which the effects of object induced X-ray attenuation are reduced in the X-ray image data.

35. A system as defined in claim 34, wherein the image of the piece of luggage rendered on the display device includes an overlay image conveying a position of the detected object.

36. A system as defined in claim 16, wherein determining the threat status of the piece of luggage includes processing the compensated X-ray image data with an automated threat detection engine to determine if the piece of luggage contains prohibited objects.

37. A system as defined in claim 16, wherein the detected object includes any one of a laptop computer, an electronic device and a handle bar.

38. A non-transitory computer readable storage medium as defined in claim 18, wherein simulating interactions between the detected object and X-rays includes generating the virtual model of the object.

39. A non-transitory computer readable storage medium as defined in claim 18, wherein detecting the object in the piece of luggage includes processing the X-ray image data to identify object characterization features.

40. A non-transitory computer readable storage medium as defined in claim 18, wherein detecting the object in the piece of luggage includes processing a user input signal conveying a location corresponding to the object in an image of the piece of luggage derived based on the X-ray image data.

41. A non-transitory computer readable storage medium as defined in claim 18, wherein deriving information for use in determining the threat status of the piece of luggage includes:
   a) processing the X-ray image data to render the image of the piece of luggage on a display device;
   b) providing a control for allowing a user to select the location corresponding to the object on the rendered image of the piece of luggage.

42. A non-transitory computer readable storage medium as defined in claim 18, wherein deriving the compensated X-ray image data includes:
   a) identifying a portion of the X-ray image data corresponding to the detected object;
   b) reducing in the identified portion of the X-ray image data effects of object induced X-ray attenuation resulting from X-rays travelling through the detected object based at least in part on the derived X-ray signature associated with the detected object.

43. A non-transitory computer readable storage medium as defined in claim 18, wherein determining the threat status of the piece of luggage includes processing the compensated X-ray image data to render an image of the piece of luggage on a display to assist an operator in determining if the piece of luggage contains prohibited objects.

44. A non-transitory computer readable storage medium as defined in claim 43, wherein the method caused to be executed by the computing device comprises providing a user activated control for transmitting command signals to the computing device, the computing device being responsive to the command signals to alter a degree to which the effects of object induced X-ray attenuation are reduced in the X-ray image data.

45. A non-transitory computer readable storage medium as defined in claim 44, wherein the image of the piece of luggage rendered on the display device includes an overlay image conveying a position of the detected object.

46. A non-transitory computer readable storage medium as defined in claim 18, wherein determining the threat status of the piece of luggage includes processing the compensated X-ray image data with an automated threat detection engine to determine if the piece of luggage contains prohibited objects.

47. A system as defined in claim 26, wherein said system includes a display device in communication with said output and wherein the data conveying results obtained by the computing system released at said output causes said display device to render the compensated X-ray image of the piece of luggage to assist an operator in determining if the piece of luggage contains prohibited objects.

48. A system as defined in claim 26, wherein deriving information for use in determining the threat status of the piece of luggage includes processing the compensated X-ray image of the piece of luggage with an automated threat detection engine to determine if the piece of luggage contains prohibited objects.

49. A system as defined in claim 26, wherein removing from the X-ray image at least part of the depiction of the object includes generating the virtual model of the object.

50. A system as defined in claim 26, wherein the object whose depiction was detected in the X-ray image of the piece of luggage includes any one of a laptop computer, an electronic device and handle bar.

51. A non-transitory computer readable storage medium as defined in claim 27, wherein deriving information for use in determining the threat status of the piece of luggage includes processing the compensated X-ray image of the piece of luggage with an automated threat detection engine to determine if the piece of luggage contains prohibited objects.

52. A non-transitory computer readable storage medium as defined in claim 27, wherein removing from the X-ray image at least part of the depiction of the object includes generating the virtual model of the object.

\* \* \* \* \*